US010899687B2

(12) United States Patent
Gandelman et al.

(10) Patent No.: US 10,899,687 B2
(45) Date of Patent: Jan. 26, 2021

(54) PROCESS FOR THE PREPARATION OF ORGANIC HALIDES

(71) Applicant: Technion Research & Development Foundation Limited, Haifa (IL)

(72) Inventors: Mark Gandelman, Kfar-Sava (IL); Gennady Nisnevich, Haifa (IL); Kseniya Kulbitski, Haifa (IL); Alexander Artaryan, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 356 days.

(21) Appl. No.: 15/763,848

(22) PCT Filed: Oct. 6, 2016

(86) PCT No.: PCT/IL2016/051084
§ 371 (c)(1),
(2) Date: Mar. 28, 2018

(87) PCT Pub. No.: WO2017/060906
PCT Pub. Date: Apr. 13, 2017

(65) Prior Publication Data
US 2018/0282247 A1 Oct. 4, 2018

Related U.S. Application Data

(60) Provisional application No. 62/238,208, filed on Oct. 7, 2015.

(51) Int. Cl.
| | |
|---|---|
| *C07C 17/363* | (2006.01) |
| *C07C 25/06* | (2006.01) |
| *C07C 25/08* | (2006.01) |
| *C07C 25/10* | (2006.01) |
| *C07C 25/13* | (2006.01) |
| *C07C 201/12* | (2006.01) |
| *C07C 253/30* | (2006.01) |
| *C07B 39/00* | (2006.01) |
| *C07C 19/01* | (2006.01) |
| *C07C 25/02* | (2006.01) |
| *C07C 205/08* | (2006.01) |
| *C07C 205/12* | (2006.01) |
| *C07C 205/37* | (2006.01) |
| *C07C 255/50* | (2006.01) |
| *C07D 307/89* | (2006.01) |

(52) U.S. Cl.
CPC ............ *C07C 17/363* (2013.01); *C07B 39/00* (2013.01); *C07C 19/01* (2013.01); *C07C 25/02* (2013.01); *C07C 25/06* (2013.01); *C07C 25/08* (2013.01); *C07C 25/10* (2013.01); *C07C 25/13* (2013.01); *C07C 201/12* (2013.01); *C07C 205/08* (2013.01); *C07C 205/12* (2013.01); *C07C 205/37* (2013.01); *C07C 253/30* (2013.01); *C07C 255/50* (2013.01); *C07D 307/89* (2013.01)

(58) Field of Classification Search
CPC .................................................. C07C 17/363
See application file for complete search history.

(56) References Cited

FOREIGN PATENT DOCUMENTS

IN 803DEL1999 6/2005
WO WO 2011154953 A1 12/2011

OTHER PUBLICATIONS

Johnson, R. G. "The Degradation of Carboxylic Acid Salts by Means of Halogen—The Hunsdiecker Reaction" Chem. Rev. 1956, 56, 219 (Year: 1956).*
Derek H.R. Barton et al. "The invention of new radical chain reactions. Part VIII. Radical chemistry of thiohydroxamic esters; A new method for the generation of carbon radicals from carboxylic acids" Barton et al., Tetrahedron vol. 41, Issue 19, 1985, pp. 3901-3924.
Derek H.R. Barton et al., The invention of radical reactions: Part XVI. Radical decarboxylative bromination and iodination of aromatic acids, Tetrahedron, vol. 43, Issue 19, 1987, pp. 4321-4328.
D. Naskar; et al., "1-Haloalkynes from Propiolic Acids: A Novel Catalytic Halodecarboxylation Protocol", Journal of Organic Chemistry, (Oct. 8, 1999), vol. 64, ISSN 0022-3263, pp. 6896-6897, XP 002656405 [A].
D. Naskar; et al., "Catalytic Hunsdiecker Reaction and One-Pot Catalytic Hunsdiecker-Heck Strategy: Synthesis of alpha,beta-Unsaturated Aromatic Halides, alpha-(Dihalomethyl) benzenemethanols, 5-Aryl-2,4-pentadienoic acids, Dienoates and Dienamides", Tetrahdron, (20000000), vol. 56, ISSN 0040-4020, pp. 1369-1377, XP 002656408 [A].
F.G. Bordwell et al., "Synthesis of Dihalomethyl and alpha-Haloalkyl Sulfones by the Halogenative Decarboxylation of alpha-Aryl- and alpha-Alkylsulfonylakanecarboxylic Acids", Journal of Organic Chemistry, (Jan. 1, 1974), vol. 39, ISSN 0022-3263, pp. 2516-2519, XP055521306 [A].
Hiromi Hamamoto et al., Hypervalent Iodine(III)-LiX Combination in Fluoroalcohol Solvent for Aromatic Halogenation of Electron-Rich Arenecarboxylic Acids Synlett 2011(11): 1563-1566.
International Search Report for PCT application No. PCT/IL2016/051083, dated Oct. 6, 2016.
International Search Report for PCT application No. PCT/IL2016/051084, dated Dec. 21, 2016.
Jaya Prakash Das, and Sujit Roy,"Catalysynthetic Hunsdiecker Reaction of α,β-Unsaturated Carboxylic Acids: How Efficient Is the Catalyst?", J. Org. Chem., 2002, 67 (22), pp. 7861-7864.

(Continued)

*Primary Examiner* — Medhanit W Bahta
(74) *Attorney, Agent, or Firm* — Mark S. Cohen; Pearl Cohen; Zedek Latzer Baratz LLP

(57) ABSTRACT

The present invention provides a halo-de-carboxylation process for the preparation of organic chlorides, organic bromides and mixtures thereof, from their corresponding carboxylic acids, using a chlorinating agent selected from trichloroisocyanuric acid (TCCA), dichloroisocyanuric acid (DCCA), or combination thereof, and a brominating agent.

28 Claims, No Drawings

(56) References Cited

OTHER PUBLICATIONS

John A. Davis, et al., "Modifications of the Hunsdiecker Reaction", J. Org. hem., 1965, 30 (2), pp. 415-417.

J. Braz. Chem. Soc. "Oxidative Dehydration of Glycerol to Acrylic Acid over Vanadium-Impregnated Zeolite Beta", 2013, v. 24, 213.

Kristin Janz and Neelu Kaila, Bromodecarboxylation of Quinoline Salicylic Acids: Increasing the Diversity of Accessible Substituted Quinolines, J. Org. Chem., 2009, 74 (22), pp. 8874-8877.

Leonardo S. de Almeida et al., "Tribromoisocyanuric Acid in Trifluoroacetic Acid: An Efficient System for Smooth Brominating of Moderately Deactivated Arenes", Synlett 2013 v. 24, 603-606.

Leonardo R. Sodre et al. "A Green Hunsdiecker Reaction of Cinnamic Acids", Journal of Brazilian Chemical Society, vol. 24, No. 2, Jan. 1, 2013, pp. 212-218, XP55572808.

Martin Brzozowski et al., Synthesis of substituted 4-(1H-indol-6-yl)-1H-indazoles as potential PDK1 inhibitors,Tetrahedron vol. 70, Issue 2, Jan. 14, 2014, pp. 318-326.

W Gottardi—Monatshefte fur Chemie Chemical Monthly, 1968, v. 99, pp. 815-822.

N.J. Bunce and N.G. Murray, "On the relationship between the Hunsdiecker and Simonini reactions", Tetrahedron 1971, v. 27, 5323-5335.

Pelayo Camps et al., "Hunsdiecker-Type Bromodecarboxylation of Carboxylic Acids with Iodosobenzene Diacetate-Bromine", Tetrahedron 2000, v. 56, 2703-2707.

Randy W.Jackson et al., The discovery and structure-activity relationships of pyrano[3,4-b]indole-based inhibitors of hepatitis C virus NS5B polymerase, Bioorg. Med. Chem. Lett. 2011, v. 21, 3227-3231.

S. Chowdhury; et al., "The First Example of a Catalytic Hunsdiecker Reaction: Synthesis of beta-Halostyrenes", Journal of Organic Chemistry, (Jan. 1, 1977), vol. 62, ISSN 0022-3263, pp. 199-200, XP 002656406 [A].

Supplementary European Search Report for EP 16853205 dated Mar. 22, 2019.

Supplementary European Search Report for EP 16853206 dated Apr. 9, 2019.

Yong Luo et al., "Silver-catalyzed decarboxylative halogenation of carboxylic acids", Tetrahedron Letters 2010, vol. 51, Issue 50, Dec. 15, 2010, pp. 6646-6648.

Zejiang Li, Kunkai Wang, Zhong-Quan Liu, "Transition-Metal-Free Hunsdiecker Reaction of Electron-Rich Arenecarboxylic Acids and Aryl Aldehydes in Water", Synlett 2014; 25(17): 2508-2512.

Johnson, R. G., & Ingham, R. K. (1956). The degradation of carboxylic acid salts by means of halogen—The Hunsdiecker reaction. *Chemical Reviews*, 56(2), 219-269.

* cited by examiner

PROCESS FOR THE PREPARATION OF ORGANIC HALIDES

CROSS-REFERENCE TO RELATED APPLICATIONS

This application is a National Phase Application of PCT International Application No. PCT/IL2016/051084, International Filing Date Oct. 6, 2016, claiming priority of U.S. Provisional Patent Application No. 62/238,208, filed Oct. 7, 2015, which is hereby incorporated by reference.

FIELD OF THE INVENTION

The present invention provides a halo-de-carboxylation process for the preparation of organic chlorides, organic bromides and mixtures thereof, from their corresponding carboxylic acids, using a chlorinating agent selected from trichloroisocyanuric acid (TCCA), dichloroisocyanuric acid (DCCA), or any combination thereof, and a brominating agent. The invention further provides a composition comprising a carboxylic acid, brominating agent and chlorinating agent selected from trichloroisocyanuric acid (TCCA), dichloroisocyanuric acid (DCCA), or combination thereof.

BACKGROUND OF THE INVENTION

Organic bromides and chlorides are stable compounds which are used commercially for many applications, such as pharmaceuticals, agriculture, disinfectants, flame extinguishing agents, and dyes. The organic halides have found wide use in numerous industrial applications as chemical intermediates for the production of other commercial organic compounds. (*Ullmann's Encyclopedia of Industrial Chemistry* 2012, v. 6, 331-358; v. 8, 483-519).

Carboxylic acids are widely available and cheap raw materials in the organic synthesis. Therefore, the oxidative decarboxylation of carboxylic acids with concomitant replacement by halogen (halo-de-carboxylation) is an extremely useful alternative for regioselective syntheses of organic halides.

The Hunsdiecker reaction (*Tetrahedron* 1971, v. 27, 5323) is a halo-de-carboxylation reaction, which utilizes treatment of anhydrous silver salt of organic carboxylic acid with molecular bromine or chlorine in an inert solvent (*Tetrahedron* 1971, v. 27, 5323). However, the reaction is extremely sensitive to presence of trace amounts of water, which lead to the recovery of unreacted acid. Another way to perform the Hunsdiecker reaction is by using a mixture of organic carboxylic acid and Br$_2$/HgO (*J. Org. Chem.* 1965, v. 30, 415) instead of the silver salt.

Accordingly, the Hunsdiecker reaction and/or its modifications, use heavy metal salts such as those of silver and mercury, therefore the disadvantages of such procedures for the pharmaceutical industry are obvious.

The Barton halo-de-carboxylation procedure (Barton et al., *Tetrahedron* 1985, v. 41, 3901; 1987, v. 43, 4321) is directed to the conversion of organic carboxylic acids to the esters of N-hydroxypyridine-2-thione. The thiohydroxamic esters are halogenated by XCCl$_3$, wherein X is Cl or Br. Thiopyridines are formed in the reaction as co-products.

Additional process for converting carboxylic acids to their corresponding bromides is by treating the carboxylic acid with (diacetoxyiodo)benzene and bromine or LiBr as bromine source (*Tetrahedron* 2000, v. 56, 2703; *Synlett* 2011, 1563). However, in this reaction, it is difficult to separate the desired product from iodobenzene, which is formed as co-product in the reaction.

A bromo- and chlorodecarboxylation of aromatic carboxylic acids using CuBr$_2$ and CuCl$_2$ as the halogen sources has been developed by Wu et. al. (*Tetrahedron Letters* 2010, v. 51, 6646) and Liu et. al. (*Tetrahedron Letters* 2013, v. 54, 3079), which also utilize the use of heavy metals in their reactions.

Another example for bromodecarboxylation utilizes the reagent system 1205-KBr for bromodecarboxylation of electron-rich arenecarboxylic acids (*Synlett* 2014, v. 25, 2508). This method, however, is limited to preparation of specific brominated phenol ether derivatives.

N-Bromo and N-chloro amides such as N-bromosuccinimide (*Chem. Pharm. Bull.* 2002, v. 50, 941), 1,3-dibromo-5,5-dimethylhydantoin (*Bioorg. Med. Chem.* 2008, v. 16, 10001; *Bioorg. Med. Chem. Lett.* 2011, v. 21, 3227; *Tetrahedron* 2014, v. 70, 318), dibromoisocyanuric acid (*Monatsh. Chem.* 1968, v. 99, 815; 1969, v. 100, 42 & 1977, v. 108, 1067), tribromoisocyanuric acid (*Synlett* 2013, v. 24, 603), trichloroisocyanuric acid (TCCA) (*JOC* 1970, v. 35, 719) N-chlorosuccinimide (NCS) (*ACS Med. Chem. Lett.* 2010, v. 1, 30; *Chem. Pharm. Bull.* 2002, v. 50, 941; *Org. Proc. R&D* 2010, 14, 1254) are useful reagents for the electrophilic halogenation of aromatic carboxylic acids in the meta-position with respect to the carboxylic group. However, the use of these reagents in halo-de-carboxylation reactions is limited.

For example, reaction of N-bromosuccinimide with arenecarboxylic acids, predominantly electron-rich arenecarboxylic acids, yields bromoarenenes (*IN803DEL*1999; *JOC* 2009, v. 74, 8874; *Tetrahedron Lett.* 2007, v. 48, 5429). Reaction of aryl acrylic and propiolic acids with N-halosuccinimides (*JOC* 2002, v. 67, 7861) and trihaloisocyanuric acids (*J. Braz. Chem. Soc.* 2013, v. 24, 213) yields aryl vinyl and ethynyl halides. All of these reactions are heterolytic reactions that do not require initiation with radical initiators or UV-visible light irradiation.

The conversion of carboxylic acid, R—CO$_2$H, to their corresponding halide, R—X, is therefore a rather difficult transformation. There is a need for the development of new strategies for halo-de-carboxylation.

SUMMARY OF THE INVENTION

In one embodiment, this invention is directed to a process for the preparation of organic halide of formula (1A) from a carboxylic acid of formula (2A) represented by scheme 1:

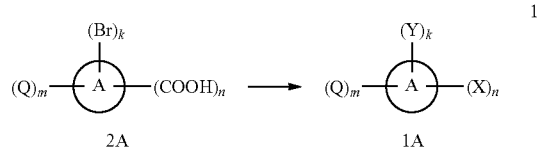

said process comprises radical halo-de-carboxylation reaction comprising reacting carboxylic acid (2A) with a chloroisocyanurate and a brominating agent to yield organic halide (1A);
wherein
said chloroisocyanurate is trichloroisocyanuric acid, dichloroisocyanuric acid, or any combination thereof;
A is arene, alkane, cycloalkane or saturated heterocycle;
n is an integer greater than or equal to 1;
X is Cl or Br; wherein if n>1, then X may be the same or different;
k is an integer greater than or equal to 0;
Y is Cl or Br; wherein if k>1, then Y may be the same or different;
m is an integer greater than or equal to 0;
each Q is independently F, Cl, Br, $R^1$, acyl, C(O)$R^1$, C(O)O$R^1$, C(O)Cl, C(O)N($R^1$)$_2$, CN, SO$_2$$R^1$, SO$_3$$R^1$, NO$_2$, N($R^1$)$_3^+$, O$R^1$, OCF$_3$, O-acyl, OC(O)$R^1$, OSO$_2$$R^1$, S$R^1$, S-acyl, SC(O)$R^1$, N($R^1$)acyl, N($R^1$)C(O)$R^1$, N($R^1$)SO$_2$$R^1$, N(acyl)$_2$, N[C(O)$R^1$]SO$_2$$R^1$, N[C(O)$R^1$]$_2$, CF$_3$; or any two vicinal Q substituents are joined to form a 5- or 6-membered substituted or unsubstituted, saturated or unsaturated carbocyclic or heterocyclic ring;
wherein each $R^1$ is independently aryl, alkyl, cycloalkyl or heterocyclyl, wherein said $R^1$ is optionally substituted by one or more substituents of $R^2$;
wherein each $R^2$ is independently F, Cl, Br, COOH, acyl, aryl, alkyl, cycloalkyl or heterocyclyl; wherein if either one of $R^2$ in (2A) is carboxylic group COOH, then the respective $R^2$ in (1A) is Br or Cl;
wherein the position of said X, Y and Q in said structure of formula (1A) correspond to the same position of said COOH, Br and Q, respectively in said structure of formula (2A).

In one embodiment, this invention is directed to a process for the preparation of haloarene of formula (1B)

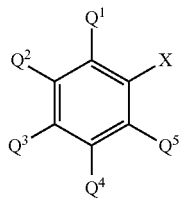

1B from a arenecarboxylic acid of formula (2B),

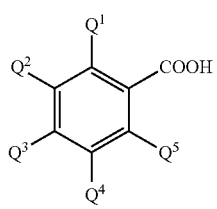

2B wherein said process comprises radical halo-de-carboxylation reaction comprising reacting (2B) with a chloroisocyanurate and a brominating agent to yield haloarene (1B);
wherein,
said chloroisocyanurate is trichloroisocyanuric acid, dichloroisocyanuric acid, or any combination thereof wherein
X is Cl or Br;
wherein $Q^1$, $Q^2$, $Q^3$, $Q^4$, and $Q^5$, are each independently selected from: H, F, Cl, Br, $R^1$, COOH, acyl, C(O)$R^1$, C(O)O$R^1$, C(O)Cl, C(O)N($R^1$)$_2$, CN, SO$_2$$R^1$, SO$_3$$R^1$, NO$_2$, N($R^1$)$_3^+$, O$R^1$, OCF$_3$, O-acyl, OC(O)$R^1$, OSO$_2$$R^1$, S$R^1$, S-acyl, SC(O)$R^1$, N($R^1$)acyl, N($R^1$)C(O)$R^2$, N($R^1$)SO$_2$$R^1$, N(acyl)$_2$, N[C(O)$R^1$]SO$_2$$R^1$, N[C(O)$R^1$]$_2$, CF$_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;
wherein each $R^1$ is independently aryl, alkyl, cycloalkyl or heterocyclyl wherein $R^1$ is optionally substituted by one or more substituents of $R^2$;
wherein each $R^2$ is independently F, Cl, Br, COOH, acyl, aryl, alkyl, cycloalkyl or heterocyclyl;
wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Cl or Br;
wherein if either one of $Q^1$, $Q^2$, $Q^3$, $Q^4$, $Q^5$, and/or $R^2$ in (2B) is bromine (Br) then the respective $Q^1$, $Q^2$, $Q^3$, $Q^4$, $Q^5$, and/or $R^2$ in (1B) is Cl or Br.

In one embodiment, this invention is directed to a radiation-sensitive composition comprising a carboxylic acid (2A)

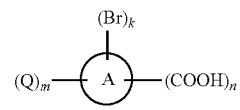

2A a chloroisocyanurate and a brominating agent which generates organic halide (1A)

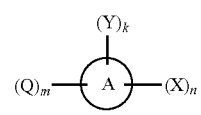

1A upon electromagnetic irradiation,
wherein
said chloroisocyanurate is trichloroisocyanuric acid, dichloroisocyanuric acid, or any combination thereof;
A is arene, branched alkane, cycloalkane or saturated heterocycle;
n is an integer greater than or equal to 1;
m is an integer greater than or equal to 0;
X is Cl or Br; wherein if n>1, then X may be the same or different;
k is an integer greater than or equal to 0;
Y is Cl or Br; wherein if k>1, then Y may be the same or different;
each Q is independently F, Cl, Br, $R^1$, acyl, C(O)$R^1$, C(O)O$R^1$, C(O)OMe, C(O)Cl, C(O)N($R^1$)$_2$, CN, SO$_2$$R^1$, SO$_3$$R^1$, NO$_2$, N($R^1$)$_3^+$, O$R^1$, OCF$_3$, O-acyl, OC(O)$R^1$, OSO$_2$$R^1$, S$R^1$, S-acyl, SC(O)$R^1$, N($R^1$)acyl, N($R^1$)C(O)$R^1$, N($R^1$)SO$_2$$R^1$, N(acyl)$_2$, N[C(O)$R^1$]SO$_2$$R^1$, N[C(O)$R^1$]$_2$, CF$_3$; or any two vicinal Q substituents are joined to form a 5- or 6-membered substituted or unsubstituted, saturated or unsaturated carbocyclic or heterocyclic ring;
wherein each $R^1$ is independently aryl, alkyl, cycloalkyl or heterocyclyl, wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $R^2$ in (2A) is a carboxylic group COOH, then the respective $R^2$ in (1A) is Br or Cl;

wherein the position of said Br and Q in said structure of formula (1A) correspond to the same position of said COOH and Q, respectively in said structure of formula (2A).

In one embodiment, the process and composition of this invention comprises a brominating agent. In another embodiment, the brominating agent is $Br_2$ (bromine), a salt comprising bromide or a polybromide anion and an organic or inorganic cation; or any combination thereof.

In one embodiment, the process of this invention is conducted in the presence of an organic or inorganic solvent and the composition of this invention comprises an organic or inorganic solvent. In another embodiment, the inorganic solvent is $CO_2$, $SO_2$, $SO_2Cl_2$ or combination thereof. In another embodiment, the solvent is $CH_3CN$, $CH_3NO_2$, an ester, a hydrocarbon solvent, or halocarbon solvent or combination thereof. In another embodiment, the hydrocarbon solvent is $C_6H_6$. In another embodiment, the halocarbon solvent is $CH_2Cl_2$, $Cl(CH_2)_2Cl$, $CHCl_3$, $CCl_4$, $C_6H_5Cl$, o-$C_6H_4Cl_2$, $BrCCl_3$, $CH_2Br_2$, $CFCl_3$, $CF_3CCl_3$, $ClCF_2CFCl_2$, $BrCF_2CFClBr$, $CF_3CClBr_2$, $CF_3CHBrCl$, $C_6H_5F$, $C_6H_5CF_3$, 4-$ClC_6H_4CF_3$, 2,4-$Cl_2C_6H_3CF_3$ or any combination thereof.

In one embodiment, the process and composition of this invention comprises and is further subjected to electromagnetic irradiation. In another embodiment, the electromagnetic irradiation is microwave, infrared, ultraviolet, or visible light irradiation or any combination thereof. In another embodiment, the electromagnetic irradiation is visible light irradiation. In another embodiment, the source of said visible light is sunlight, fluorescent lamp, light-emitting diode, incandescent lamp or any combination thereof.

In one embodiment, the process and composition of this invention comprises a brominating agent and a carboxylic acid compound of formula (2A) or (2B). In another embodiment, the molar ratio between brominating agent/(each carboxylic group of said carboxylic acid compound) is between 0.1 and 4.

In one embodiment, the process and composition of this invention comprises chloroisocyanurate and a carboxylic acid compound of formula (2A) or (2B). In another embodiment, the molar ratio between the chloroisocyanurate/(each carboxylic group of the carboxylic acid compound) is between 0.1 and 2.

In another embodiment, the process of this invention is conducted at a temperature of between about −20° C. and about 200° C. In another embodiment, the process of this invention is conducted at a temperature of between about 0° C. and about 150° C.

In another embodiment, the process is conducted in the presence of radical initiator. In another embodiment, the radical initiator is an azo compound or organic peroxide.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention is directed to a process for the preparation of organic halide of formula (1A) from a carboxylic acid of formula (2A) represented by scheme 1:

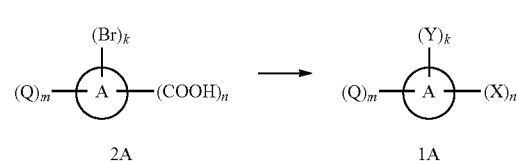

said process comprises radical halo-de-carboxylation reaction comprising reacting carboxylic acid (2A) with a chloroisocyanurate and a brominating agent to yield organic halide (1A);

wherein said chloroisocyanurate is trichloroisocyanuric acid, dichloroisocyanuric acid, or any combination thereof;

A is arene, alkane, cycloalkane or saturated heterocycle;

n is an integer greater than or equal to 1;

m is an integer greater than or equal to 0;

X is Cl or Br; wherein if n>1, then X may be the same or different;

k is an integer greater than or equal to 0;

Y is Cl or Br; wherein if k>1, then Y may be the same or different; each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;

wherein each $R^1$ is independently aryl, alkyl, cycloalkyl or heterocyclyl, wherein said $R^1$ is optionally substituted by one or more substituents of $R^2$;

wherein each $R^2$ is independently F, Cl, Br, COOH, acyl, aryl, alkyl, cycloalkyl or heterocyclyl; wherein if either one of $R^2$ in (2A) is carboxylic group COOH, then the respective $R^2$ in (1A) is Br or Cl;

wherein the position of said X, Y and Q in said structure of formula (1A) correspond to the same position of said COOH, Br and Q, respectively in said structure of formula (2A).

In one embodiment, this invention is directed to a process for the preparation of organic halide of formula (1B) from a carboxylic acid of formula (2B) represented by scheme 2:

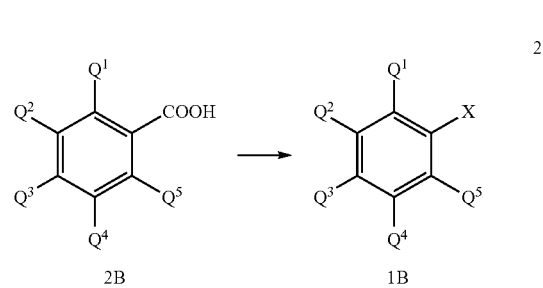

wherein said process comprises radical halo-de-carboxylation reaction comprising reacting (2B) with a chloroisocyanurate and a brominating agent to yield haloarene (1B); wherein, said chloroisocyanurate is trichloroisocyanuric acid, dichloroisocyanuric acid, or any combination thereof wherein X is Cl or Br;

wherein $Q^1$, $Q^2$, $Q^3$, $Q^4$, and $Q^5$, are each independently selected from: H, F, Cl, Br, $R^1$, COOH, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;

wherein each $R^1$ is independently aryl, alkyl, cycloalkyl or heterocyclyl wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Cl or Br;

wherein if either one of $Q^1$, $Q^2$, $Q^3$, $Q^4$, $Q^5$, and/or $R^2$ in (2B) is bromine (Br) then the respective $Q^1$, $Q^2$, $Q^3$, $Q^4$, $Q^5$, and/or $R^2$ in (1B) is Cl or Br.

In one embodiment, the organic halide, (1A) or (1B) that is formed in the process of this invention is a mixture of the respective chloride and bromide of each compound. In another embodiment, the organic halide of formula (1A) is a mixture of organic halide products of formula (1A) with different X groups; if k is different than 0, then the organic halide products optionally have also different Y group. In another embodiment, the organic halide of formula (1B) is a mixture of organic halide products of formula (1B) with different X groups; if $Q^1$, $Q^2$, $Q^3$, $Q^4$, $Q^5$ is Cl or Br, then the organic halide products optionally are a mixture of different halo groups (Cl or Br).

In one embodiment, A of the organic halide (1A) and of the carboxylic acid (2A) in scheme 1 is arene. In another embodiment, A of the organic halide (1A) and the carboxylic acid (2A) in scheme 1 is a alkane. In another embodiment, A of the organic halide (1A) and the carboxylic acid (2A) in scheme 1 is a linear alkane. In another embodiment, A of the organic halide (1A) and the carboxylic acid (2A) in scheme 1 is a branched alkane. In another embodiment, A of the organic halide (1A) and of the carboxylic acid (2A) in scheme 1 is a cycloalkane. In another embodiment, A of the organic halide (1A) and of the carboxylic acid (2A) in scheme 1 is a saturated heterocycle.

In one embodiment the A is substituted with one or more substituents Q (in Scheme 1); where each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;

wherein each $R^1$ is independently aryl, alkyl, cycloalkyl or heterocyclyl, wherein $R^1$ is optionally substituted by one or more substituents of $R^2$;

wherein each $R^2$ is independently F, Cl, Br, COOH, acyl, aryl, alkyl, cycloalkyl or heterocyclyl.

In another embodiment, each Q is independently Cl. In another embodiment, each Q is independently F. In another embodiment, each Q is independently Br. In another embodiment, each Q is independently CN. In another embodiment, each Q is independently $CF_3$. In another embodiment, each Q is independently $CCl_3$. In another embodiment, each Q is independently acyl group. In another embodiment, each Q is independently $SO_3R^1$. In another embodiment, each Q is independently $SO_2R^1$. In another embodiment, each Q is independently $C(O)R^1$. In another embodiment, each Q is independently $C(O)OR^1$. In another embodiment, each Q is independently C(O)OMe. In another embodiment, each Q is independently COCl. In another embodiment, each Q is independently amide. In another embodiment, each Q is independently $C(O)N(R^1)_2$. In another embodiment, each Q is independently $OCF_3$. In another embodiment, each Q is independently $R^1$. In another embodiment, each Q is independently alkyl. In another embodiment, each Q is independently t-Bu. In another embodiment, each Q is independently cycloalkyl. In another embodiment, each Q is independently heterocyclyl. In another embodiment, each Q is independently $OR^1$. In another embodiment, each Q is independently OMe. In another embodiment, each Q is independently $SR^1$. In another embodiment, each Q is independently SMe. In another embodiment, each Q is independently acetyl. In another embodiment, each Q is independently benzoyl. In another embodiment, each Q is independently mesyl. In another embodiment, each Q is independently tosyl. In another embodiment, each Q is independently $NO_2$. In another embodiment, each Q is independently $N(R^1)_3^+$. In another embodiment, each Q is independently O-acyl. In another embodiment, each Q is independently $OC(O)R^1$. In another embodiment, each Q is independently acetoxy. In another embodiment, each Q is independently $OSO_2R^1$. In another embodiment, each Q is independently mesyloxy. In another embodiment, each Q is independently tosyloxy. In another embodiment, each Q is independently S-acyl. In another embodiment, each Q is independently $SC(O)R^1$. In another embodiment, each Q is independently $N(R^1)$acyl. In another embodiment, each Q is independently $N(R^1)C(O)R^1$. In another embodiment, each Q is independently $N(R^1)SO_2R^1$. In another embodiment, each Q is independently $N(acyl)_2$. In another embodiment, each Q is independently $N[C(O)R^1]SO_2R^1$. In another embodiment, each Q is independently saccharinyl. In another embodiment, each Q is independently $N[C(O)R^1]_2$. In another embodiment, each Q is independently phthalimido. In another embodiment, each Q is independently aryl. In another embodiment, each Q is independently $C_6H_5$. In another embodiment, each Q is independently $C_6F_5$. In another embodiment, two vicinal Q substituents are joined to form a 5- or 6-membered substituted or unsubstituted, saturated or unsaturated heterocyclic ring. In another embodiment, two vicinal Q substituents are joined to form dihydrofuran-2,5-dione. In another embodiment, two vicinal Q substituents are joined to form pyrrolidine-2,5-dione. In another embodiment, if m>1 then Q substituents are the same. In another embodiment, if m>1 then Q substituents are different.

In one embodiment, A of the organic bromide (1A) and of the carboxylic acid (2A) in scheme 1 is a benzene. In another embodiment, A is cycloalkane. In another embodiment, A is a saturated heterocycle.

In another embodiment A of the organic bromide (1A) and of the carboxylic acid (2A) in scheme 1 is an alkane. In another embodiment, the alkane chain is linear. In another embodiment, the alkane chain is branched.

In one embodiment, the carboxylic acid (2A) in scheme 1 and the carboxylic acid (2B) in scheme 2 is not ECH(Z)—COOH, wherein E is acyl, $CO_2Z'$, $SO_2Z'$, $S(Z')_2^+$, or $N(Z')_3^+$ and Z and Z' are each independently a hydrogen, alkyl or an aryl. In another embodiment, the carboxylic acid (2A) in scheme 1 and the carboxylic acid (2B) in scheme 2 is not ZCH═CH—COOH or ZC≡C—COOH, where Z is either a hydrogen, alkyl or an aryl, the latter two are optionally substituted.

In another embodiment, the A in scheme 1 is not unsaturated heterocycle. In another embodiment, the A in scheme 1 is not alkene or alkyne. In another embodiment, the A in scheme 1 is not cycloalkene or cycloalkyne. In another embodiment, the Q in scheme 1 is not OH, $NH_2$, NHR, or $NR^2$ group.

In another embodiment, at least one of $Q^1$, $Q^2$, $Q^3$, $Q^4$, and/or $Q^5$ is F, Cl, Br, $CF_3$, $CCl_3$, CN, COOH, C(O)OMe, $NO_2$, phthalimide, $OCF_3$, and/or any two of $Q^1$ and $Q^2$, $Q^2$ and $Q^3$, $Q^3$ and $Q^4$, or $Q^4$ and $Q^5$, are joined to form a dihydrofuran-2,5-dione or pyrrolidine-2,5-dione ring.

In another embodiment, at least one of $Q^1$, $Q^2$, $Q^3$, $Q^4$, and $Q^5$ is $NO_2$. In another embodiment, at least one of $Q^1$, $Q^2$, $Q^3$, $Q^4$, and $Q^5$ is $CF_3$. In another embodiment, at least one of $Q^1$, $Q^2$, $Q^3$, $Q^4$, and $Q^5$ is CN. In another embodiment, at least one of $Q^1$, $Q^2$, $Q^3$, $Q^4$, and $Q^5$ is Cl. In another embodiment, at least one of $Q^1$, $Q^2$, $Q^3$, $Q^4$, and $Q^5$ is F. In another embodiment, at least one of $Q^1$, $Q^2$, $Q^3$, $Q^4$, and $Q^5$ is Br. In another embodiment, at least one of $Q^1$, $Q^2$, $Q^3$, $Q^4$, and $Q^5$ is phthalimide. In another embodiment, at least one of $Q^1$, $Q^2$, $Q^3$, $Q^4$, and $Q^5$ is C(O)OMe.

In one embodiment, $Q^1$ of formula (1B) and (2B) in scheme 2 is F. In another embodiment, $Q^1$ is H. In another embodiment, $Q^1$ is $CF_3$. In another embodiment, $Q_1$ is Cl. In another embodiment, $Q^1$ is Br. In another embodiment, $Q^1$ is $NO_2$. In another embodiment, $Q^1$ is $CO_2Me$. In another embodiment, $Q^1$ is phthalimide.

In one embodiment, $Q^2$ of formula (1B) and (2B) in scheme 2 is H. In another embodiment, $Q^2$ is F. In another embodiment, $Q^2$ is $CF_3$. In another embodiment, $Q^2$ is Cl. In another embodiment, $Q^2$ is Br. In another embodiment, $Q^2$ is CN. In another embodiment, $Q^2$ is $NO_2$. In another embodiment, $Q^2$ is $CO_2Me$. In another embodiment, $Q^2$ is COOH.

In one embodiment, $Q^3$ of formula (1B) and (2B) in scheme 2 is H. In another embodiment, $Q^3$ is CN. In another embodiment, $Q_3$ is Cl. In another embodiment, $Q^3$ is Br. In another embodiment, $Q^3$ is F. In another embodiment, $Q^3$ is $CF_3$. In another embodiment, $Q^3$ is $NO_2$. In another embodiment, $Q^3$ is $CO_2Me$. In another embodiment, $Q^3$ is COOH.

In one embodiment, $Q^4$ of formula (1B) and (2B) in scheme 2 is H. In another embodiment, $Q^4$ is F. In another embodiment, $Q^4$ is $CF_3$. In another embodiment, $Q^4$ is CN. In another embodiment, $Q^4$ is Cl. In another embodiment, $Q^4$ is $NO_2$.

In one embodiment, $Q^5$ of formula (1B) and (2B) in scheme 2 is H. In another embodiment, $Q^5$ is F. In another embodiment, $Q^5$ is $CF_3$. In another embodiment, $Q^5$ is CN. In another embodiment, $Q^5$ is Cl.

In one embodiment, $Q^3$ and $Q^4$ of formula (1B) and (2B) in scheme 2 are joined to form a 5- or 6-membered substituted or unsubstituted, saturated or unsaturated heterocyclic ring. In another embodiment, the heterocyclic ring is dihydrofuran-2,5-dione. In another embodiment, the heterocyclic ring is pyrrolidine-2,5-dione. In another embodiment, the heterocyclic ring is substituted with an alkyl. In another embodiment, the alkyl is t-Bu.

In one embodiment, X of scheme 1 and of compounds (1A) and (1B) is Br or Cl. In another embodiment X is Cl. In another embodiment X is Br.

In one embodiment, Y of scheme 1 and of compounds (1A) is Br or Cl. In another embodiment Y is Cl. In another embodiment Y is Br.

In another embodiment, the compound of formula (1A) or (1B) comprises a both Cl and Br. In another embodiment, the process Scheme 1 or Scheme 2 yields a mixture of products of formula (1A) or (1B) wherein each product has different halo groups.

In one embodiment, m of scheme 1 and of compounds (1A) and (2A) is an integer number greater than or equal to 0. In another embodiment, m is 0. In another embodiment, m is 1. In another embodiment, m is 2. In another embodiment, m is 3. In another embodiment, if m>1 than Q can be different or the same.

In one embodiment, n of compounds (1A), (2A) in scheme 1 is an integer number greater than or equal to 1. In another embodiment, n is between 1 and 5. In another embodiment, n is between 1 and 3. In another embodiment, n is 1 or 2. In another embodiment, n is 1. In another embodiment, n is 2. In another embodiment, n is 3. In one embodiment if n>1, then X may be the same or different.

In one embodiment, k of scheme 1 and of compounds (1A) and (2A) is an integer number greater than or equal to 0. In another embodiment, k is 0. In another embodiment, k is 1. In another embodiment, k is 2. In another embodiment, k is 3. In another embodiment, if k>1 than Y may be the same or different.

In one embodiment, this invention is directed to a process for the preparation of organic halides from its corresponding carboxylic acid, said process comprises a radical halo-decarboxylation reaction of the carboxylic acid with a chloroisocyanurate and a brominating agent, wherein said carboxylic acid is selected from the carboxylic acids listed in Tables 2, 3, 4 and 7 below.

In one embodiment, X and Y of the organic halide (1A) are bromine atoms when A is an alkane, cycloalkane or saturated heterocycle.

In one embodiment, X of the organic halide (1A) is a bromine atom if Q is a nitro group. In one embodiment, X of the organic halide (1B) is a bromine atom if either one of $Q^1$, $Q^2$, $Q^3$, $Q^4$, $Q^5$ is a nitro group.

In one embodiment, X of the organic halide (1A) is a chlorine atom if Q is different than a nitro group. In one embodiment, X of the organic halide (1B) is a chlorine atom if none of the substituents $Q^1$, $Q^2$, $Q^3$, $Q^4$ and $Q^5$ are a nitro group.

In one embodiment, if either one of $Q^1$, $Q^2$, $Q^3$, $Q^4$, or $Q^5$ in arenecarboxylic acid (2B) is Br then the respective $Q^1$, $Q^2$, $Q^3$, $Q^4$, or $Q^5$ in haloarene (1B) is Cl.

In one embodiment, the process of this invention, represented by schemes 1 and 2, has a radical mechanism. In another embodiment all factors that promote radical reaction may stimulate the process of this invention. Factors that promote radical reaction: heating, electromagnetic irradiation, addition of radical initiators.

In one embodiment, the process and composition of this invention comprises chloroisocyanurate. In another embodiment, the chloroisocyanurate is trichloroisocyanuric acid (TCCA) dichloroisocyanuric acid (DCCA), salts thereof or any combination thereof.

In one embodiment, the process of this invention and the composition of this invention make use and comprises a brominating agent. In another embodiment, the brominating agent is bromine, a salt comprising bromide or a polybromide anion and an organic or inorganic cation; or any combination thereof.

In another embodiment, the cation is a substituted or unsubstituted onium ion. The term "onium" refers in one embodiment to cations (with their counter-ions) derived by addition of a hydron to a mononuclear parent hydride of the nitrogen, chalcogen and halogen families. Non limiting examples of oniums include $[NH_4]^+$ ammonium, $[OH_3]^+$ oxonium, $[PH_4]^+$ phosphonium, $[SH_3]^+$ sulfonium, $[AsH_4]^+$ arsonium, $[SeH_3]^+$ selenonium, $[BrH_2]^+$ bromonium, $[SbH_4]^+$ stibonium, $[TeH_3]^+)$ telluronium, $[IH2]^+$ iodonium, $[BiH_4]^+$ bismuthonium.

Substituted oniums refers to substitution of the above parent ions by univalent groups or by two or three free valencies. E.g. $[SMe_3]^+$ trimethylsulfonium (a tertiary sulfonium ion), $[MePPh_3]^+$ methyltriphethylphosphonium (a quaternary phosphonium ion), $[HNEt_3]^+$ triethylammonium (a tertiary ammonium ion), $[NPr_4]^+$ tetrapropylammonium (a quaternary ammonium ion), $[R_2C=NR_2]^+$ iminium ions.

In one embodiment, the term "inorganic cation" used herein refers to an alkali or alkaline earth metal cations, transition metal cation, or unsubstituted onium cation. In another embodiment, the inorganic cation is $Li^+$. In another embodiment, the inorganic cation is $Na^+$. In another embodiment, the inorganic cation is $K^+$. In another embodiment, the inorganic cation is $Rb^+$. In another embodiment, the inorganic cation is $Cs^+$. In another embodiment, the inorganic cation is $Zn^{2+}$. In another embodiment, the inorganic cation is $Cu^{2+}$. In another embodiment, the inorganic cation is ammonium cation $[NH_4]^+$.

In one embodiment, the term "organic cation" used herein refers to substituted onium cation. In another embodiment, the substituted onium cation is substituted ammonium cation, substituted phosphonium cation, substituted oxonium cation, substituted sulfonium cation, substituted arsonium cation, substituted selenonium cation, substituted telluronium cation, substituted iodonium cation, any other known onium cation, or any combination thereof. In another embodiment, the substituted ammonium cation is the substituted or unsubstituted guanidinium cation, substituted or unsubstituted pyridinium cation, substituted or unsubstituted amidinium cation, substituted or unsubstituted quaternary ammonium cation $[NR^1_4]^+$, substituted or unsubstituted tertiary ammonium cation $[HNR^1_3]^+$. In another embodiment, the substituted phosphonium cation is substituted or unsubstituted quaternary phosphonium cation $[PR^1_4]^+$; wherein $R^1$ is alkyl, aryl, cycloalkyl, heterocyclyl, or any combination thereof. In another embodiment, the quaternary ammonium cation $[NR^1_4]^+$ is tetraalkylammonium, trialkylarylammonium, dialkyldiarylammonium, trialkylbenzylammonium, or any combination thereof. In another embodiment, non-limiting examples of the quaternary ammonium cation $[NR^1_4]^+$ include tetrametylammonium, tetraethylammonium, tetrabutylammonium, tetraoctylammonium, trimethyloctylammonium, cetyltrimethylammonium, or any combination thereof. In another embodiment, the quaternary phosphonium cation $[PR^1_4]^+$ is tetraalkylphosphonium, alkyltriarylphosphonium, benzyltriarylphosphonium, benzyltrialkylphosphonium, or any combination thereof. In another embodiment, non-limiting examples of the quaternary phosphonium cation $[PR^1_4]^+$ include tetraphenylphosphonium, benzyltriphenylphosphonium, tetrabutylphosphonium, methyltriphenylphosphonium, benzyltributylphosphonium cation or any combination thereof. In another embodiment, the substituted sulfonium cation is substituted or unsubstituted tertiary sulfonium cation, substituted or unsubstituted sulfoxonium, thiopyrylium or thiuronium ion; or any combination thereof. In another embodiment the substituted oxonium cation is substituted or unsubstituted tertiary oxonium cation, substituted or unsubstituted pyrylium cation; or any combination thereof. In another embodiment, substituted cations as referred herein are substituted with halide, nitrile, nitro, alkyl, aryl, cycloalkyl, heterocyclyl, amide, carboxylic acid, acyl or any combination thereof.

In one embodiment, the term "polybromide anion" used herein refers to a molecule or ion containing three or more bromine atoms or to an ion of formula $[Br_p]^{q-}$, where p is an integer of at least 3 and q is an integer of at least 1 and not more than p/2. In another embodiment, p is an integer between 3-24 and q is 1 or 2. In another embodiment p is 3, 5, 7, 9, 11 or 13 and q is 1. In another embodiment p is 4, 8, 20 or 24 and q is 2.

In another embodiment, the brominating agent is $Br_2$, $Bu_4NBr$, $Bu_4NBr_3$, or any combination thereof.

An "alkyl" refers, in one embodiment, to a univalent groups derived from alkanes by removal of a hydrogen atom from any carbon atom: $C_nH_{2n+1}$—. In one embodiment, the alkyl group has 1-20 carbons. Examples for alkyls include but are not limited to: methyl, ethyl, propyl, isopropyl, butyl, isobutyl, s-butyl, tert-butyl, pentyl, neopentyl, octyl, isooctyl and the like The term "alkane" refers to acyclic branched or unbranched hydrocarbons having the general formula $C_nH_{2n+2}$, and therefore consisting entirely of hydrogen atoms and saturated carbon atoms. Examples of alkane include: methane, ethane, propane, n-butane, isobutane, n-pentane, neopentane, n-octane, isooctane and the like.

An "arene" refers to monocyclic and polycyclic aromatic hydrocarbons. Nonlimiting examples of arenes are benzene, biphenyl, naphthalene, anthracene, and the like.

An "aryl" group refers, to univalent groups derived from arenes by removal of a hydrogen atom from a ring carbon atom. Nonlimiting examples of aryl groups are phenyl, naphthyl, antracenyl, phenanthryl, and the like.

A "cycloalkyl" refers to univalent groups derived from cycloalkanes by removal of a hydrogen atom from a ring carbon atom Non limiting examples of cycloalkyl include: cyclobutyl, norbornyl, cyclopentyl and cyclohexyl.

A "cycloalkane" refers to saturated mono- or polycyclic hydrocarbons. A general chemical formula for cycloalkanes would be $C_nH_{2(n+1-g)}$ where n=number of C atoms and g=number of rings in the molecule.

A "heterocyclyl" refers to univalent groups formed by removing a hydrogen atom from any ring atom of a mono or polycyclic heterocyclic compound.

A "heterocycle" refers to a mono- or poly-cyclic heterocyclic compound consisting of carbon, hydrogen and at least one of nitrogen, sulfur, oxygen, phosphorous or combination thereof in one of the rings. In one embodiment, the heterocyclic compound consists 2-7 fused rings. Non limiting examples of monocyclic saturated heterocyclic compounds are aziridine, oxirane, thiirane, azetidine, oxetane, thietane, pyrrolidine, tetrahydrofurane, thiolane, pyperidine, oxane, thiane, azepane, oxepane, thiepane, imidazolidine, oxazolidine, thiazolidine, dioxolane, piperazine, morpholine, dioxane, homopiperazine. Non limiting examples of saturated bicyclic heterocyclic compounds are quinuclidine, 7-oxanorbornane, 7-thiabicyclo[2.2.1]heptane, 3-oxabicyclo [3.1.1]heptane, 3-azabicyclo[3.1.1]heptane, octahydroindole, octahydro-2-benzofuran.

An "amide" refers, in one embodiment, to a derivative of oxoacid in which an acidic hydroxyl group has been replaced by an amino or substituted amino group. Compounds having one or two acyl groups on a given nitrogen are generically included and may be designated as primary and secondary amides, respectively.

An "acyl" group is formed by removing one or more hydroxyl groups from oxoacids, and replacement analogues of such acyl groups. E.g. —C(=O)R, —C(=O)OR, —C(=O)NR$_2$, —C≡N, —S(=O)$_2$R, —S(=O)$_2$OR, —NO$_2$. Non limiting examples of the acyl groups include acetyl —C(O)Me, benzoyl —C(O)Ph, C(O)OMe, —C(=O)Cl, mesyl MeSO$_2$—, tosyl 4-MeC$_6$H$_4$SO$_2$.

A "carboxylic acid" refers, in one embodiment, to oxoacids having the structure RC(=O)OH.

In another embodiment, the halo-de-carboxylation reaction represented by schemes 1 and 2 is conducted at room temperature. In another embodiment, the reaction is conducted under cooling. In another embodiment, the halo-de-carboxylation reaction is initiated thermally. In another embodiment, the halo-de-carboxylation reaction is further subjected to heat. In another embodiment, the halo-de-carboxylation reaction is conducted at a temperature of between −20° C. and 200° C. In another embodiment, said process is conducted at a temperature of between about 0° C. and about 150° C.

In another embodiment, the process of this invention further comprising the use of radical initiator in the reaction. In another embodiment, the radical initiator is an azo compound or organic peroxide. In another embodiment, the azo compound is azobisisobutyronitrile (AIBN) or 1,1'-azobis(cyclohexanecarbonitrile) (ABCN). In another embodiment, the organic peroxide is benzoyl peroxide.

In another embodiment, the bromoarene of formula (1A) and/or (1B) is prepared according to process described in Examples 1-14.

In one embodiment, the process of this invention, represented by schemes 1 and 2, is conducted under electromagnetic irradiation. In another embodiment, the electromagnetic radiation is visible light, infrared radiation, ultraviolet radiation, microwave radiation or any combination thereof.

In another embodiment, the source of the visible light is sunlight, fluorescent lamp, light-emitting diode, incandescent lamp or any combination thereof.

The term "irradiation" refers in one embodiment to the energy that is irradiated or transmitted in the form of rays or waves or particles. Electromagnetic irradiation refers to radiation consisting of waves of energy associated with electric and magnetic fields resulting from the acceleration of an electric charge. Ultrasound refers to cyclic mechanical vibrations with a frequency greater than 20 kilohertz (20,000 hertz). Ultraviolet irradiation refers to electromagnetic radiation with wavelengths 100 to 400 nm. Visible irradiation (light, visible light) refers to electromagnetic irradiation with wavelengths 400 to 780 nm. Infrared irradiation refers to electromagnetic irradiation with wavelengths 780 to 20000 nm. Microwave irradiation refers to electromagnetic irradiation with wavelengths 2 to 1000 mm.

Devices serving as a source of the electromagnetic irradiation include a mercury lamp, a xenon lamp, a carbon arc lamp, an incandescent lamp, a tungsten lamp, a fluorescent lamp, light-emitting diode, and sunlight, and the like.

Tungsten lamp refers to incandescent lamp that generates light by passing an electric current through a thin filament wire (usually of wolfram) until it is extremely hot. The lamps are often filled by a halogen gas such as iodine and bromine that allow filaments to work at higher temperatures and higher efficiencies.

Light-emitting diode (LED) refers to a semiconductor (often a combination of gallium, arsenic, and phosphorous or gallium and nitrogen) containing an n region (where electrons are more numerous than positive charges) separated from a p region (where positive charges are more numerous than negative charges). Upon application of a voltage, charges move and emission of ultraviolet, visible, or infrared radiation is produced each time a charge recombination takes place. Although an LED emits incoherent monochromatic light, normally a very narrow frequency range is obtained.

In another embodiment, the process is conducted in the presence of an organic or inorganic solvent and the composition of this invention comprises an organic or inorganic solvent. In another embodiment, the inorganic solvent is $CO_2$, $SO_2$, $SO_2Cl_2$ or combination thereof. In another embodiment, the organic solvent is $CH_3CN$, $CH_3NO_2$, an ester, a hydrocarbon solvent, or halocarbon solvent or combination thereof. In another embodiment the halocarbon solvent is $CH_2Cl_2$, $Cl(CH_2)_2Cl$, $CHCl_3$, $CCl_4$, $C_6H_5Cl$, o-$C_6H_4Cl_2$, $BrCCl_3$, $CH_2Br_2$, $CFCl_3$, $CF_3CCl_3$, $ClCF_2CFCl_2$, $BrCF_2CFClBr$, $CF_3CClBr_2$, $CF_3CHBrCl$, $C_6H_5F$, $C_6H_5CF_3$, 4-$ClC_6H_4CF_3$, 2,4-$Cl_2C_6H_3CF_3$ or any combination thereof. In another embodiment, the solvent is $CH_2Cl_2$. In another embodiment, the solvent is a polar solvent. In another embodiment, the solvent is a nonpolar solvent. In another embodiment, the solvent is a hydrocarbon. In another embodiment, the solvent is benzene $C_6H_6$ (PhH). In another embodiment, the solvent is acetonitrile $CH_3CN$ (MeCN). In another embodiment, the solvent is ethyl acetate EtOAc. In another embodiment, the solvent is halocarbon. In another embodiment, the solvent is $CCl_4$. In another embodiment, the solvent is chloroform $CHCl_3$. In another embodiment, the solvent is $BrCCl_3$. In another embodiment, the solvent is $CH_2Br_2$. In another embodiment, the solvent is $CFCl_3$. In another embodiment, the solvent is $CF_3CCl_3$. In another embodiment, the solvent is $ClCF_2CFCl_2$. In another embodiment, the solvent is $BrCF_2CFClBr$. In another embodiment, the solvent is $CF_3CClBr_2$. In another embodiment, the solvent is halothane $CF_3CHBrCl$. In another embodiment, the solvent is $C_6H_5F$. In another embodiment, the solvent is chlorobenzene $C_6H_5Cl$ (PhCl). In another embodiment, the solvent is benzotrifluoride $C_6H_5CF_3$ (PhCF$_3$). In another embodiment, the solvent is 4-$ClC_6H_4CF_3$. In another embodiment, the solvent is 1,2-dichloroethane $Cl(CH_2)_2Cl$ (DCE). In another embodiment, the solvent is ortho-dichlorobenzene o-$C_6H_4Cl_2$. In another embodiment, the solvent is dichloromethane $CH_2Cl_2$ (DCM). In another embodiment, the solvent is 2,4-dichlorobenzotrifluoride 2,4-$Cl_2C_6H_3CF_3$. In another embodiment, bromodecarboxylation process is preferably conducted in a halocarbon solvent. In another embodiment, bromodecarboxylation process is preferably conducted in a $BrCCl_3$, $CH_2Cl_2$, $CH_2Br_2$, $CF_3CHBrCl$ or any combination thereof.

The term "hydrocarbon solvent" refers to any solvent consisting of the carbon and hydrogen elements. Non limiting examples of hydrocarbon solvents are cyclohexane, heptane, pentane, hexane, or benzene $C_6H_6$.

The term "halocarbon solvent" refers to any solvent wherein one or more of the carbons are covalently linked to one or more halogens (fluorine, chlorine, or bromine). Non limiting examples of halocarbon solvents are chloroform $CHCl_3$, dichloromethane $CH_2Cl_2$ (DCM), bromotrichloromethane $BrCCl_3$, chlorobenzene $C_6H_5Cl$ (PhCl), ortho-dichlorobenzene o-$C_6H_4Cl_2$, 1,2-dichloroethane $Cl(CH_2)_2Cl$ (DCE), carbon tetrachloride $CCl_4$, 1,3-dichloropropane Cl(CH$_2$)$_3$Cl, 1,1,2,2-tertrachlorodifluoroethane FCCl$_2$CCl$_2$F, 1,1,2-trichloroethane CHCl$_2$CH$_2$Cl, trichloroethylene Cl$_2$C=CHCl, perchloroethylene Cl$_2$C=CCl$_2$, bromobenzene C$_6$H$_5$Br, 1,1,2-trichlorotrifluoroethane, dibromomethane CH$_2$Br$_2$, 2-bromo-2-chloro-1,1,1-trifluoroethane CF$_3$CHBrCl (halothane), 1,2-dibromoethane Br(CH$_2$)$_2$Br, benzotrifluoride C$_6$H$_5$CF$_3$ (PhCF$_3$), 2,4-dichlorobenzotrifluoride 2,4-Cl$_2$C$_6$H$_3$CF$_3$.

In one embodiment, the process of this invention, represented by schemes 1 and 2 is conducted in the presence of electromagnetic irradiation. In another embodiment, the shorter the time of the reaction, the larger the obtained amount of the bromide product with respect to the chloride. In another embodiment, the longer the time of the reaction, the larger the obtained amount of the chloride product with respect to the bromide. In one embodiment, when the process is conducted for a time less than 1 h, the major product is the bromide. In another embodiment, when the process is conducted for a time longer than 3 h, the major product is the chloride.

In one embodiment, following the formation of organic halide, or the compound of formula (1A) or (1B) the organic halide is isolated from the reaction mixture by filtration, washing, chromatography, crystallization or any combination thereof. In one embodiment, following the formation of R—X, R—X is isolated from the reaction mixture by filtration, washing, chromatography, crystallization or any combination thereof. In another embodiment the compound of formula (1A) or (1B) is isolated from the reaction mixture by filtration followed by a washing step. In another embodiment the washing step comprises washing with an aqueous reducing agent followed by washing with an aqueous base. In another embodiment the washing step comprises washing with an aqueous base followed by washing with an aqueous reducing agent. In another embodiment, the washing step comprises washing with an aqueous reducing agent and a base.

In one embodiment the bromide compound, chloride compound of formula (1A) or (1B) or mixture thereof is isolated from the reaction mixture by a washing step.

In another embodiment, the washing step comprises treating of the reaction mixture with reducing agent, wherein excess of the chloroisocyanurate is converted to cyanuric acid insoluble in non-polar organic solvents, and thereby can be removed from the organic phase. In another embodiment, an aqueous reducing agent refers to an aqueous solution comprising a reducing agent. Non limiting examples of reducing agents are Na$_2$SO$_3$, NaHSO$_3$, Na$_2$S$_2$O$_3$, NaBH$_4$/NaOH or combination thereof. In another embodiment the reducing agent is added at a concentration of between 1-10% w/w to the water to obtain an aqueous reducing agent solution.

In one embodiment, the process of this invention directed to halo-de-carboxylation comprising a washing step with an aqueous reducing agent. In another embodiment, following the washing step a potassium iodide starch paper test is performed to identify traces of the bromo reagent. "A potassium iodide starch paper test" (SPT) refers to a starch iodide test paper that has been wetted with aqueous acetic acid; 1:1; v/v]. In another embodiment, if the test is positive, an additional aqueous reducing agent is added to the reaction mixture.

In another embodiment the washing step comprises washing the product with a mild aqueous base wherein the unreacted carboxylic acid is removed from the organic phase by washing with an aqueous base. In another embodiment, the carboxylic acid is recovered by acidifying the aqueous phase. In another embodiment, an aqueous base refers to an aqueous solution comprising a base. Non limiting examples of a base is NaHCO$_3$, NaOH, Na$_2$CO$_3$, KOH, Na$_2$SO$_3$ or combination thereof. In another embodiment the base is added at a concentration of between 1-10% w/w to the water to obtain an aqueous base solution.

In another embodiment, the washing step with an aqueous reducing agent is conducted before the washing step with the aqueous base. In another embodiment, the washing step with the aqueous base is conducted before the washing step with the aqueous reducing agent. In another embodiment, the washing step comprises washing with an aqueous reducing agent and a base.

Such a combination of an aqueous reducing agent and a base includes Na$_2$SO$_3$ and NaBH$_4$/NaOH which are basic reducing agents that combine properties of reducing agent and a base.

In another embodiment, the washing steps of this invention are conducted using the organic solvent of the reaction mixture as the organic phase. In another embodiment, the washing step with the aqueous base and the washing step with the aqueous reducing agent are independently performed using a) the organic solvent of the reaction mixture, b) a mixture of organic solvents, or c) a different organic solvent, as the organic phase. Non limiting examples of organic solvents used as an organic phase in the washing step are hydrocarbon solvent, halocarbon solvent, or esters such as cyclohexane, heptane, hexane, pentane, benzene, toluene, chlorobenzene, 1,2-dichloroethane, carbon tetrachloride, 1,3-dichloropropane, 1,2,2-tertrachlorodifluoroethane, 1,2-trichloroethane, trichloroethylene, perchloroethylene, dichloromethane, chloroform, ethyl acetate or butyl acetate.

In one embodiment, following the washing step, the aqueous phase is treated with an acid or an aqueous acid solution to precipitate solid cyanuric acid.

In one embodiment, the organic halide product of the halo-de-carboxylation reaction is soluble in organic phase and not soluble in the aqueous phase. In another embodiment, the crude organic bromide is isolated from reaction mixture by standard organic solvent extractive work-up.

In one embodiment, removing the solvent from the organic phase gives the crude desired halide (1A) or (1B) (where X is Br or Cl), or a mixture thereof as the residue. In another embodiment, the residue is the pure desired halide (1A) or (1B). In another embodiment, the residue is the pure desired bromide (1A) or (1B) (wherein X is Br). In another embodiment, the residue is the pure desired chloride (1A) or (1B) (wherein X is Cl). In another embodiment, the halide is purified by crystallization, rectification or chromatography of the residue.

In another embodiment the isolation and purification further comprises a drying step. In another embodiment the purification further comprises chromatography.

In one embodiment, the process of this invention provides a process for the preparation of pure organic halide. In another embodiment, the process of this invention provides a process for the preparation of pure organic chloride. In another embodiment, the process of this invention provides a process for the preparation of pure organic bromide. In another embodiment, the process of this invention provides a process for the preparation of mixtures of organic chloride and organic bromide.

In another embodiment, the "pure halide", "pure chloride" or "pure bromide" refers to 92% or more purity. In another embodiment, the "pure halide", "pure chloride" or "pure bromide" refers to about 95% or more purity. In another embodiment, the "pure halide", "pure chloride" or "pure bromide" refers to about 90% or more purity. In another embodiment, the "pure halide", "pure chloride" or "pure bromide" refers to about 85% or more purity. In another embodiment, the "pure halide", "pure chloride" or "pure bromide" refers to about 99% or more purity. In another embodiment, the "pure halide", "pure chloride" or "pure bromide" refers to about 98% or more purity. In another embodiment, the "pure halide", "pure chloride" or "pure bromide" refers to about 97% or more purity In one embodiment, this invention is directed to organic halide compound represented by the formula (1A) or (1B) having purity of about 99% or more, prepared according to the process of this invention. In another embodiment, this invention is directed to organic halide compound represented by the formula (1A) or (1B) having purity of about 98% or more prepared according to the process of this invention. In another embodiment, this invention is directed to organic halide compound represented by the formula (1A) or (1B) having purity of about 90% or more, prepared according to the process of this invention. In another embodiment, this invention is directed to organic halide compound represented by the formula (1A) or (1B) having purity of about 95% or more, prepared according to the process of this invention. In another embodiment, this invention is directed to organic halide compound represented by the formula (1A) or (1B) having purity of about 85% or more, prepared according to the process of this invention. In another embodiment, this invention is directed to organic halide compound represented by the formula (1A) or (1B) having purity of about 97% or more, prepared according to the process of this invention. In another embodiment, X is Cl. In another embodiment, X is Br.

In one embodiment, the process of this invention, represented by schemes 1 and 2, provides a yield of 60% or more. In another embodiment, the process of this invention provides a yield of 70% or more. In another embodiment, the process of this invention provides a yield of 80% or more. In another embodiment, the process of this invention provides a yield of 85% or more. In another embodiment, the process of this invention provides a yield of 90% or more. In another embodiment, the process of this invention provides a yield of 95% or more.

In one embodiment, this invention is directed to a process and composition comprising carboxylic acid, chloroisocyanurate and brominating agent in a certain molar ratio.

In one embodiment the chloroisocyanurate:(each carboxylic group of said carboxylic acid of formula (2A)) molar ratio is between 0.1 and 2. In another embodiment the chloroisocyanurate:(each carboxylic group of the carboxylic acid of formula (2A)) molar ratio is between 1 and 2. In another embodiment the chloroisocyanurate:(each carboxylic group of the carboxylic acid of formula (2A)) molar ratio is between 0.1 and 1. In another embodiment the chloroisocyanurate:(each carboxylic group of the carboxylic acid of formula (2A)) molar ratio is 1. In another embodiment the chloroisocyanurate:(each carboxylic group of the carboxylic acid of formula (2A)) molar ratio is between 1 and 1.5.

In one embodiment, the reaction mixture of the process according to this invention, further comprises a brominating agent. In another embodiment, the brominating agent:(each carboxylic group of the carboxylic acid of formula (2A)) molar ration is between 0.1 and 4. In another embodiment, brominating agent:(each carboxylic group of the carboxylic acid of formula (2A)) molar ration is between 1 and 4. In another embodiment, the brominating agent:(each carboxylic group of the carboxylic acid of formula (2A)) molar ration is between 0.1 and 2. In another embodiment, the brominating agent:(each carboxylic group of the carboxylic acid of formula (2A)) molar ration is between 0.1 and 1. In another embodiment the brominating agent:(each carboxylic group of the carboxylic acid of formula (2A)) molar ration is between 1 and 2. In another embodiment the brominating agent:((each carboxylic group of the carboxylic acid of formula (2A)) molar ration is between 1 and 3

In one embodiment, this invention is directed to a radiation-sensitive composition comprising a carboxylic acid (2A)

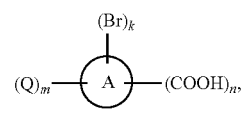

a chloroisocyanurate and a brominating agent which generates organic halide (1A)

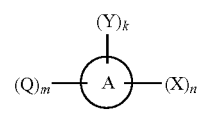

upon electromagnetic irradiation, wherein said chloroisocyanurate is trichloroisocyanuric acid, dichloroisocyanuric acid, or any combination thereof;

A is arene, branched alkane, cycloalkane or saturated heterocycle;

n is an integer greater than or equal to 1;

X is Cl or Br; wherein if n>1, then X may be the same or different;

k is an integer greater than or equal to 0;

Y is Cl or Br; wherein if k>1, then Y may be the same or different;

m is an integer greater than or equal to 0;

each Q is independently F, Cl, Br, $R^1$, acyl, $C(O)R^1$, $C(O)OR^1$, $C(O)OMe$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;

wherein each $R^1$ is independently aryl, alkyl, cycloalkyl or heterocyclyl, wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $R^2$ in (2A) is a carboxylic group COOH, then the respective $R^2$ in (1A) is Br or Cl;

wherein the position of said Br and Q in said structure of formula (1A) correspond to the same position of said COOH and Q, respectively in said structure of formula (2A).

In another embodiment, this invention is directed to a radiation-sensitive composition comprising a carboxylic acid, chloroisocyanurate and a brominating agent; wherein said carboxylic acid is represented by the structure of compound (2B):

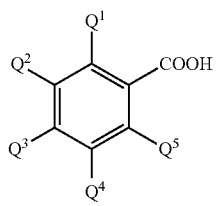

2B which generates organic halide (1B)

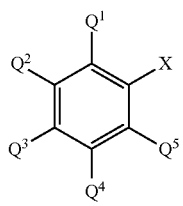

1B upon electromagnetic irradiation,
wherein
X is Cl or Br;
wherein $Q^1$, $Q^2$, $Q^3$, $Q^4$, and $Q^5$, are each independently selected from: H, F, Cl, Br, $R^1$, COOH, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;

wherein each $R^1$ is independently aryl, alkyl, cycloalkyl or heterocyclyl wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Cl or Br;

wherein if either one of $Q^1$, $Q^2$, $Q^3$, $Q^4$, $Q^5$, and/or $R^2$ in (2B) is bromine (Br) then the respective $Q^1$, $Q^2$, $Q^3$, $Q^4$, $Q^5$, and/or $R^2$ in (1B) is Cl or Br.

Mechanism of the Halo-De-Carboxylation Reaction of the Invention

Without bounding to any particular mechanism or theory, it is contemplated that the process according to this invention is described as follows:

i. Reaction of the brominating agent with the chloroisocyanurate to yield bromoisocyanurate and chlorinating agent, according to equation (1):

chloroisocyanurate+brominating agent→bromoisocyanurate+chlorinating agent (1)

ii. Bromination of the carboxylic acid R—CO₂H with the bromoisocyanurate of equation (1) to give the corresponding acyl hypobromite, R—CO₂Br, according to equation (2):

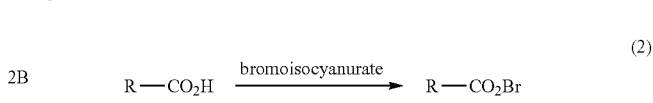

(2)

iii. Homolytic degradation of the acyl hypobromite, R—CO₂Br, to give carbon-centered free radical R. according to equation (3):

R—CO₂Br→R.+CO₂+Br. (3)

iv. R. pulls out a bromine atom from nearest bromine atom donor to yield bromide R—Br according to equation (4):

R.+bromine atom donor→R—Br (4)

wherein the bromine atom donor is selected from: Br. (equation (3)), brominating agents ($Br_2$, $Br_3^-$), or the halocarbon solvent (e.g., $BrCCl_3$, $CF_3CHBrCl$).

v. Optionally, chloro-de-bromination of the bromide R—Br with the chlorinating agent (equation 1) takes place to yield the corresponding chloride, R—Cl, and recovery the brominating agent, according to equation (5):

R—Br+chlorinating agent→R—Cl+brominating agent (5)

Another suggested mechanism for the halo-de-carboxylation of aryl-carboxylic acid according to equation (1a) is represented below:

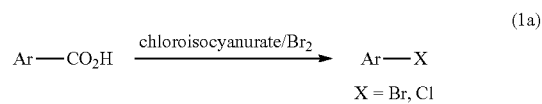

(1a)

X = Br, Cl i. Reaction of molecular bromine (brominating agent) with chloroisocyanurate to yield bromine monochloride BrCl (chlorinating agent) and bromoisocyanurate, according to equation (2a):

chloroisocyanurate+Br₂→bromoisocyanurate+BrCl (2a)

ii. Bromination of aryl-carboxylic acid Ar—CO₂H with the bromoisocyanurate to give aroyl hypobromite Ar—CO₂Br, according to equation (3a):

(3a)

iii. Homolytic degradation of the aroyl hypobromite Ar—CO₂Br to give carbon-centered free radical Ar. according to equation (4a):

Ar—CO₂Br→Ar.+CO₂+Br. (4a)

iv. Ar. pulls out a bromine atom from nearest bromine atom donor to yield aryl-bromide Ar—Br according to equation (5a):

Ar.+bromine atom donor→Ar—Br (5a)

wherein the bromine atom donor is selected from: Br. (equation (4a)), brominating agents ($Br_2$, $Br_3^-$), BrCl (equation 2a), or the halocarbon solvent (e.g., $BrCCl_3$, $CF_3CHBrCl$);

v. Optionally, radical chloro-de-bromination of the aryl-bromide, Ar—Br, takes place with bromine monochloride (chlorinating agent) to yield aryl-chloride Ar—Cl and recovery of molecular bromine (brominating agent), according to equation (6a):

Ar—Br+BrCl→Ar—Cl+$Br_2$ (6a)

A suggested mechanism for the halo-de-carboxylation reaction of alkanoic acid according to equation (1b) is described below:

(1b)

i. Reaction of tetrabutylammonium tribromide (brominating agent) with chloroisocyanurate to yield tetrabutylammonium chloride (chlorinating agent), bromine (brominating agent) and bromoisocyanurate, according to equation (2b)

chloroisocyanurate+$Bu_4NBr_3$→bromoisocyanurate+$Bu_4NCl$+$Br_2$ (2b)

ii. Bromination of alkanoic acid R—$CO_2H$ with the bromoisocyanurate to give acyl hypobromite R—$CO_2Br$, according to equation (3b):

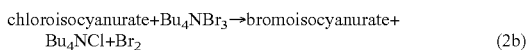
(3b)

iii. Homolytic degradation of the acyl hypobromite R—$CO_2Br$ to give carbon-centered free radical R. according to equation (4b):

R—$CO_2Br$→R.+$CO_2$+Br. (4b)

iv. R. pulls out a bromine atom from nearest bromine atom donor to yield alkyl bromide, R—Br, according to equation (5b):

R.+bromine atom donor→R—Br (5b)

v. Optionally, chloro-de-bromination of the alkyl bromide, R—Br, with tetrabutylammonium chloride (chlorinating agent) takes place to yield alkyl chloride R—Cl, and recovery tetrabutylammonium bromide (brominating agent), according to equation (6b):

R—Br+$Bu_4NCl$→R—Cl+$Bu_4NBr$ (6b).

It should be noted that the suggested mechanism presented above, is only a rough scheme of the complex real processes.

One indication for the radical chain mechanism of the halo-de-carboxylation reaction is by using a 2,2,6,6-tetramethyl-1-piperidinynyloxyl (TEMPO) carbon-centered radical scavenger as a mechanistic diagnostic tool. Addition of TEMPO as radical chain inhibitor to the initial reaction mixture of the halo-de-carboxylation reaction, inhibits the reaction. Inhibition of the halo-de-carboxylation reaction by addition of TEMPO indicates that the reaction has a radical chain mechanism.

According to the present invention, the carbon-centered free radicals R. are obtained by applying photochemical and/or thermal energy to a mixture of carboxylic acid R—$CO_2H$, chlorinating agent (e.g., chloroisocyanurate such as trichloroisocyanuric acid or dichloroisocyanuric acid) and brominating agent. The photochemical energy increases the rate of the reaction.

The term "about" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to about 5%, up to about 10% or up to about 20% of a given value.

The following examples are presented in order to more fully illustrate the preferred embodiments of the invention. They should in no way, however, be construed as limiting the broad scope of the invention.

EXAMPLES

Experimental Details

Reagents:

All reagents and solvents were purchased from Sigma-Aldrich, Alfa Aesar, Acros Organics, and TCI unless specified otherwise.

Techniques:

All reactions were performed under nitrogen atmosphere in non-flame dried glassware. Mounted nearby the reaction flask 3 W LED warm-white lamp was used for irradiation of the reaction mixture. Conversions were determined by $^1H$ NMR, and yields of isolated product refer to products with more than 95% purity by $^1H$ NMR. Flash column chromatography was performed employing 63-200 m silica gel 60 according to standard techniques (*J. Org. Chem.* 1978, v. 43, 2923).

Analytical Methods:

GC analyses were performed on Shimadzu GC-2010 gas chromatograph with flame ionization detector (FID) using a 30 m×0.25 mm Quadrex capillary column with methyl 5% phenyl silicone stationary phase, 0.25 m film thickness. For TLC analysis, Merck precoated TLC plates (silica gel 60 F-254 on glass plates, 0.25 mm) were used. NMR spectra were recorded on a Bruker AM-400 ($^1H$ at 400 MHz, $^{13}C$ at 100 MHz) instruments using $CDCl_3$ (unless otherwise stated) as a solvent. Data are reported as follows: chemical shift in ppm relative to internal TMS, multiplicity, coupling constant in Hz and integration. Compounds described in the literature were characterized by comparing their $^1H$ and/or $^{13}C$ NMR spectra to the previously reported data. New compounds were further characterized by high-resolution mass spectra.

The following abbreviations are used:
Alk=alkyl
Ar=aryl
CPT=N-chlorophthalimide
CTAB=cetyltrimethylammonium bromide
d=doublet
DCCA=dichloroisocyanuric acid
DCE=1,2-dichloroethane
DCDMH=1,3-dichloro-5,5-dimethylhydantoin
DCM=dichloromethane
FL=fluorescent room lighting
hv=visible light irradiation LL=LED lamp irradiation
m=multiplet
N-chloroamide=chloroamide, wherein chlorine atom is attached directly to nitrogen atom
NCS=N-chlorosuccinimide
NCSac=N-chlorosaccharine
NL=dark
rt=room temperature
s=singlet
SDS=sodium dodecyl sulfate
t=triplet
TL=tungsten lamp irradiation
TCCA=trichloroisocyanuric acid
Δ=heating Example 1

Chlorodecarboxylation of o-Chlorobenzoic Acid

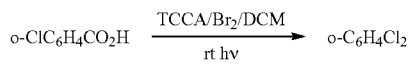

A mixture of o-chlorobenzoic acid (0.16 g, 1 mmol), TCCA (0.24 g, 1 mmol), $Br_2$ (0.64 g, 4 mmol) and DCM (10 mL) was stirred at rt under fluorescent room light irradiation for 24 h. The reaction mixture was washed with 1 M aq $Na_2SO_3$, dried over $Na_2SO_4$, filtered through short neutral alumina pad and concentrated in vacuo. The residue was dissolved in pentane, washed with 1 M aq $Na_2SO_3$, dried over $Na_2SO_4$, filtered through short neutral alumina pad and concentrated in vacuo to give o-dichlorobenzene (0.12 g, 80%).

Example 2

Bromodecarboxylation of 2-nitrobenzoic Acid

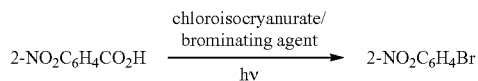

A round bottom flask equipped with Dimroth condenser (chilled to 10° C.) was charged with 2-nitrobenzoic acid (0.6 mmol), chloroisocryanurate, brominating agent and solvent (4 mL). The mixture was magnetically stirred and heated in an oil bath under fluorescent room light irradiation (FL). The cooled reaction mixture was filtered through short silica gel pad, washed with 1 M aq $Na_2SO_3$, dried over $Na_2SO_4$, and filtered. The yield of 2-nitrobromobenzene was determined by gas chromatography (GC) using 1,2,4-trichlorobenzene as internal standard. The results of the reactions are presented in Table 1:

TABLE 1

Bromodecarboxylation of 2-nitrobenzoic acid [a]

| entry | Reaction conditions | yield % [b] |
|---|---|---|
| 1 | TCCA 1 mol/$Br_2$ 2 mol/DCM, 60° FL 18 h | 4 |
| 2 | TCCA 1 mol/$Br_2$ 2 mol/$CHCl_3$, 80° FL 18 h | 92 |
| 3 | TCCA 1 mol/$Br_2$ 1 mol/$CCl_4$, 100° FL 18 h | 55 |
| 4 | TCCA 1 mol/$Br_2$ 2 mol/$CCl_4$, 100° FL 18 h | 96 |
| 5[c] | TCCA 1 mol/$Br_2$ 2 mol/$CCl_4$, 100° FL 18 h | 20 |
| 6 | TCCA 1 mol/$Br_2$ 2 mol/$CBrCl_3$, 120° FL 18 h | 97 |
| 7[c] | TCCA 1 mol/$Br_2$ 2 mol/$CBrCl_3$, 120° FL 18 h | 80 |

[a] All quantities in mole/mole of 2-nitrobenzoic acid. Oil bath temperatures in degrees Celsius.
[b] Yield is based on 2-nitrobromobenzene analyzed by GC.
[c] The reaction was provided in the absence of light.

Example 3

Bromodecarboxylation of 2-nitrobenzoic acid, 57 mmol Scale-Up

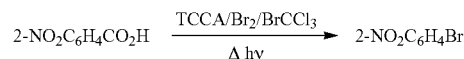

A 250 mL round bottom flask equipped with Dimroth condenser (chilled to 10° C.) was charged with 2-nitrobenzoic acid (57.1 mmol), TCCA (57.1 mmol), $Br_2$ (114 mmol) and $BrCCl_3$ (95 mL). The mixture was stirred and heated in an oil bath at 120° C. under fluorescent room light irradiation for 18 h. The cooled reaction mixture was filtered through short silica gel pad, washed with 1 M aq $Na_2SO_3$, dried over $Na_2SO_4$, filtered and concentrated in vacuo to obtain 10.6 g (92%) of 2-nitrobromobenzene.

Example 4

Bromodecarboxylation of Nitroarenecarboxylic Acids

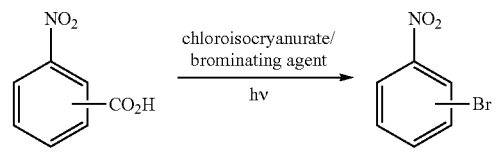

A 25 mL round bottom flask equipped with Dimroth condenser (chilled to 10° C.) was charged with nitroarenecarboxylic acid $ArCO_2H$ (1.8 mmol), chloroisocyanurate, brominating agent and solvent (8 mL). The mixture was stirred and heated in an oil bath under fluorescent room light irradiation (FL). The cooled reaction mixture was filtered through short silica gel pad, washed with 1 M aq $Na_2SO_3$, dried over $Na_2SO_4$, filtered and concentrated in vacuo to obtain bromonitroarene ArBr. The obtained product contained between 1-5% of the corresponding chloronitroarene ArCl as a by-product. The results are presented in Table 2.

TABLE 2

Bromodecarboxylation of nitroarenecarboxylic acids ArCO$_2$H [a]

| entry | ArCO$_2$H | Reaction conditions | yield % [b] |
|---|---|---|---|
| 1 | 2-NO$_2$C$_6$H$_4$CO$_2$H | TCCA 1 mol/Br$_2$ 2 mol/ CCl$_4$, 100° FL 18 h | 92 |
| 2 | 3-Cl-2-NO$_2$C$_6$H$_3$CO$_2$H | TCCA 1 mol/Br$_2$ 2 mol/ CBrCl$_3$, 120° FL 18 h | 67[c] |
| 3 | 4-Cl-2-NO$_2$C$_6$H$_3$CO$_2$H | TCCA 1 mol/Br$_2$ 2 mol/ CCl$_4$, 100° FL 18 h | 96 |
| 4 | 5-Cl-2-NO$_2$C$_6$H$_3$CO$_2$H | TCCA 1 mol/Br$_2$ 2 mol/ CCl$_4$, 100° FL 18 h | 95 |
| 5 | 4-Br-2-NO$_2$C$_6$H$_3$CO$_2$H | TCCA 1 mol/Br$_2$ 2 mol/ CCl$_4$, 100° FL 18 h | 97 |
| 6 | 2,4-(NO$_2$)$_2$C$_6$H$_3$CO$_2$H | TCCA 1 mol/Br$_2$ 2 mol/ CBrCl$_3$, 120° FL 18 h | 91 |
| 7 | 3-NO$_2$C$_6$H$_4$CO$_2$H | TCCA 1 mol/Br$_2$ 2 mol/ CCl$_4$, 100° FL 18 h | 93 |
| 8 | 4-F-3-NO$_2$C$_6$H$_3$CO$_2$H | TCCA 1 mol/Br$_2$ 2 mol/ CBrCl$_3$, 120° FL 18 h | 73[c] |
| 9 | 2-Cl-3-NO$_2$C$_6$H$_3$CO$_2$H | TCCA 1 mol/Br$_2$ 2 mol/ CBrCl$_3$, 120° FL 18 h | 85[c] |
| 10 | 4-Cl-3-NO$_2$C$_6$H$_3$CO$_2$H | TCCA 1 mol/Br$_2$ 2 mol/ CBrCl$_3$, 120° FL 18 h | 84[c] |
| 11 | 2,5-Cl$_2$-3-NO$_2$C$_6$H$_2$CO$_2$H | TCCA 1 mol/Br$_2$ 2 mol/ CBrCl$_3$, 120° FL 18 h | 92 |
| 12 | 4-NO$_2$C$_6$H$_4$CO$_2$H | TCCA 1 mol/Br$_2$ 2 mol/ CBrCl$_3$, 120° FL 18 h | 84[c] |
| 13 | 3-CF$_3$-4-NO$_2$C$_6$H$_3$CO$_2$H | TCCA 1 mol/Br$_2$ 2 mol/ CCl$_4$/CHCl$_3$[d], 100° FL 18 h | 79 |
| 14 | 2-F-4-NO$_2$C$_6$H$_3$CO$_2$H | TCCA 1 mol/Br$_2$ 2 mol/ CCl$_4$, 100° FL 18 h | 84[c] |
| 15 | 2-Cl-4-NO$_2$C$_6$H$_3$CO$_2$H | TCCA 1 mol/Br$_2$ 2 mol/ CCl$_4$/CHCl$_3$[d], 100° FL 18 h | 94 |

[a] All quantities in mole/mole of nitroarenecarboxylic acid. Oil bath temperatures in degrees Celsius.
[b] Isolated yield of bromonitroarenes ArBr.
[c] The yield was determined after purification of the product by chromatography on silica gel.
[d] Mixture of CCl$_4$ and CHCl$_3$ 4:1 v/v was used as solvent.

Entry 1: 1-bromo-2-nitrobenzene $^1$H NMR: δ 7.85-7.8 (m, 1H), 7.75-7.7 (m, 1H), 7.5-7.4 (m, 2H) ppm; $^{13}$C NMR: δ 149.8, 135.1, 133.3, 128.4, 125.6, 114.4 ppm.

Entry 2: 1-bromo-2-chloro-3-nitrobenzene $^1$H NMR: δ 7.84 (dd, J=8, 1 Hz, 1H), 7.72 (dd, J=8, 1 Hz, 1H), 7.30 (t, J=8 Hz, 1H) ppm; $^{13}$C NMR δ 149.7, 137.0, 128.2, 127.2, 125.5, 123.9 ppm.

Entry 3: 1-bromo-4-chloro-2-nitrobenzene $^1$H NMR δ 7.81 (d, J=2 Hz, 1H), 7.67 (d, J=9 Hz, 1H), 7.41 (dd, J=9, 2 Hz, 1H) ppm; $^{13}$C NMR: δ 150, 136, 134.3, 133.4, 125.7, 112.5 ppm.

Entry 4: 2-bromo-4-chloro-1-nitrobenzene $^1$H NMR δ 7.83 (d, J=9 Hz, 1H), 7.71 (d, J=2 Hz, 1H), 7.44 (dd, J=9, 2 Hz, 1H) ppm; $^{13}$C NMR: δ 148, 139.2, 134.7, 128.5, 126.7, 115.5 ppm.

Entry 5: 1,4-dibromo-2-nitrobenzene $^1$H NMR δ 7.94 (d, J=2 Hz, 1H), 7.59 (d, J=9 Hz, 1H), 7.54 (dd, J=9, 2 Hz, 1H) ppm; $^{13}$C NMR: δ 150, 136.3, 136.2, 128.5, 121.5, 113.2 ppm.

Entry 6: 1-bromo-2,4-dinitrobenzene $^1$H NMR: δ 8.64 (d, J=3 Hz, 1H), 8.29 (dd, J=9, 3 Hz, 1H), 8.02 (d, 1H, J=9 Hz) ppm; $^{13}$C NMR δ 149.7, 147.0, 136.6, 127.3, 121.9 ppm.

Entry 7: 1-bromo-3-nitrobenzene $^1$H NMR: δ 8.29 (t, J=2 Hz, 1H), 8.13 (ddd, J=8, 2, 1 Hz, 1H), 7.81 (ddd, J=8, 2, 1 Hz, 1H), 7.44 (t, J=8 Hz, 1H) ppm; $^{13}$C NMR: δ 148.6, 137.5, 130.6, 126.5, 122.7, 122.1 ppm.

Entry 8: 4-bromo-1-fluoro-2-nitrobenzene $^1$H NMR: δ 8.16 (dd, J=7, 2 Hz, 1H), 7.76 (ddd, J=9, 4, 3 Hz, 1H), 7.23 (dd, J=10, 9 Hz, 1H) ppm; $^{13}$C NMR: δ 154.6 (d, J$_{CF}$=265.9), 138.6 (d, J$_{CF}$=8 Hz), 137.8, 128.8 (d, J$_{CF}$=3 Hz), 120.2 (d, J$_{CF}$=22 Hz), 116.7 (d, J$_{CF}$=4 Hz) ppm. $^{19}$F NMR: δ-122.2 ppm.

Entry 9: 1-bromo-3-chloro-2-nitrobenzene $^1$H NMR: δ 7.58 (dd, J=8, 1 Hz, 1H), 7.47 (dd, J=8, 1 Hz, 1H), 7.32 (t, J=8 Hz, 1H) ppm; $^{13}$C NMR: δ 150.0, 132.15, 131.6, 129.7, 126.3, 113.9 ppm.

Entry 10: 4-bromo-1-chloro-2-nitrobenzene $^1$H NMR δ 8.00 (d, J=2 Hz, 1H), 7.64 (dd, J=9, 2 Hz, 1H), 7.43 (d, J=9 Hz, 1H) ppm; $^{13}$C NMR δ 148.3, 136.2, 133.1, 128.5, 126.2, 120.7 ppm.

Entry 11: 1-bromo-2,5-dichloro-3-nitrobenzene

1H NMR: δ 7.83 (d, J=2 Hz, 1H), 7.72 (d, J=2 Hz, 1H) ppm; $^{13}$C NMR δ 149.4, 136.5, 133.7, 126.07, 126.06, 124.2 ppm.

Entry 12: 1-bromo-4-nitrobenzene $^1$H NMR: δ 8.08 (d, J=9 Hz, 1H), 7.67 (d, J=9 Hz, 1H) ppm; $^{13}$C NMR: δ 147.1, 132.7, 130.1, 125.1 ppm.

Entry 13: 4-bromo-1-nitro-2-(trifluoromethyl)benzene $^1$H NMR: δ 8.5 (d, J=2 Hz, 1H), 8.26 (dd, J=9, 2 Hz, 1H), 7.96 (d, J=9 Hz, 1H) ppm; $^{13}$C NMR δ 146.9, 136.5, 131.8 (q, J$_{CF}$=33 Hz), 127.7 (d, J$_{CF}$=1 Hz), 127.5, 123.2 (q, J$_{CF}$=6 Hz), 122 (q, J$_{CF}$=274 Hz) ppm; $^{19}$F NMR: δ-66.4 ppm.

Entry 14: 1-bromo-2-fluoro-4-nitrobenzene $^1$H NMR δ 7.99-7.91 (m, 2H), 7.78 (dd, J=9, 7 Hz, 1H) ppm; $^{13}$C NMR: δ 158 (d, J$_{CF}$=252 Hz), 147.9 (d, J$_{CF}$=7 Hz), 134.3, 120.2 (d, J$_{CF}$=4 Hz), 117.3 (d, J$_{CF}$=21 Hz), 112.1 (d, J$_{CF}$=27 Hz) ppm; $^{19}$F NMR δ-105.0 ppm.

Entry 15: 1-bromo-2-chloro-4-nitrobenzene $^1$H NMR: δ 8.26 (d, J=2 Hz, 1H), 7.97 (dd, J=9, 2 Hz, 1H), 7.80 (d, J=9 Hz, 1H) ppm; $^{13}$C NMR: δ 147.3, 135.8, 134.4, 130.3, 125.1, 122.5 ppm.

Example 5

Halo-de-carboxylation of 4-methoxy-2-nitrobenzoic Acid

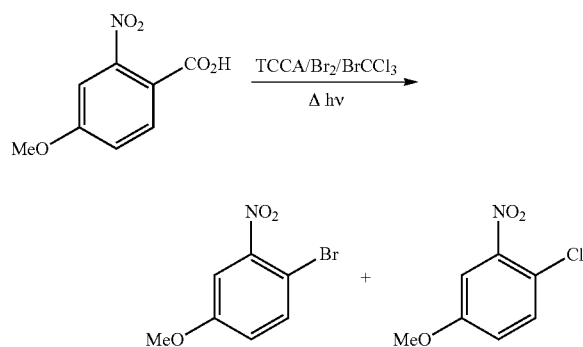

A 25 mL round bottom flask equipped with Dimroth condenser (chilled to 10° C.) was charged with 4-methoxy-2-nitrobenzoic acid (304 mg, 1.54 mmol), TCCA (357 mg, 1.54 mmol), $Br_2$ (492 mg, 3.08 mmol) and $BrCCl_3$ (8 mL). The mixture was stirred and heated in an oil bath at 120° C. under fluorescent room light irradiation for 18 h. The cooled reaction mixture was filtered through short silica gel pad, washed with 1 M aq $Na_2SO_3$, dried over $Na_2SO_4$, filtered and concentrated in vacuo. The residue was purified by chromatography on silica gel (eluent hexane/DCM) to give the mixture of 4-bromo- and 4-chloro-3-nitroanisoles (250 mg, 82:18 by GC).

Example 6

Bromodecarboxylation of Nitroarenedicarboxylic Acids

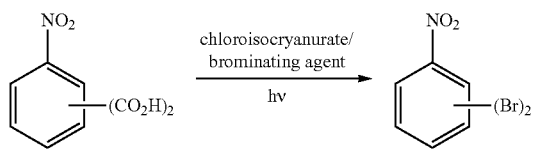

Round bottom flask equipped with Dimroth condenser (chilled to 10° C.) was charged with nitroarenedicarboxylic acid $NO_2C_6H_3(CO_2H)_2$ (0.95 mmol), chloroisocyanurate, brominating agent and solvent (8 mL). The mixture was stirred and heated in an oil bath at 120° C. under fluorescent room light irradiation. The cooled reaction mixture was filtered through short silica gel pad, washed with 1 M aq $Na_2SO_3$, dried over $Na_2SO_4$, filtered and concentrated in vacuo. The obtained dibromonitroarene $NO_2C_6H_3Br_2$ is 95-99% pure (by GC) and may contain 1-5% of corresponding monochlorinated product $NO_2C_6H_3BrCl$. The results are presented in Table 3.

TABLE 3

Bromodecarboxylation of nitroarenedicarboxylic acids $NO_2C_6H_3(CO_2H)_2$ [a]

| entry | $NO_2C_6H_3(CO_2H)_2$ | Reaction conditions | yield % [b] |
|---|---|---|---|
| 1 | 3-$NO_2$-1,2-$C_6H_3(CO_2H)_2$ | TCCA 2 mol/$Br_2$ 4 mol/$CBrCl_3$, 120° FL 60 h | 85 |
| 2 | 4-$NO_2$-1,2-$C_6H_3(CO_2H)_2$ | TCCA 2 mol/$Br_2$ 4 mol/$CBrCl_3$, 120° FL 60 h | 66 |
| 3 | 5-$NO_2$-1,3-$C_6H_3(CO_2H)_2$ | TCCA 2 mol/$Br_2$ 4 mol/$CBrCl_3$, 120° FL 60 h | 82 |

[a] All quantities in mole/mole of nitroarenedicarboxylic acid. Oil bath temperatures in degrees Celsius.
[b] Isolated yield of dibromonitroarenes $NO_2C_6H_3Br_2$ Entry 1: 1,2-dibromo-3-nitrobenzene $^1$H NMR: δ 7.84 (d, J=8 Hz, 1H), 7.63 (d, J=8 Hz, 1H), 7.33 (t, J=8 Hz, 1H) ppm; $^{13}$C NMR: δ 152.1, 136.6, 129.0, 128.0, 123.5, 117.3 ppm.

Entry 2: 1,2-dibromo-4-nitrobenzene $^1$H NMR: δ 8.42 (d, J=2 Hz, 1H), 8.00 (dd, J=9, 2 Hz, 1H), 7.80 (d, J=9 Hz, 1H) ppm; $^{13}$C NMR: 147.2, 134.3, 132.8, 128.5, 125.8, 123.1 ppm.

Entry 3: 1,3-dibromo-5-nitrobenzene $^1$H NMR: δ 8.30 (s, 2H), 8.00 (s, 1H) ppm; $^{13}$C NMR: 6149.0, 140.0, 125.6, 123.5 ppm.

Example 7

Disruption of the Halo-De-Carboxylation in the Bromination Stage

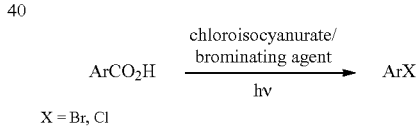

X = Br, Cl

Round bottom flask equipped with Dimroth condenser (chilled to 10° C.) was charged with arenecarboxylic acid $ArCO_2H$ (0.95 mmol), chloroisocyanurate, brominating agent and solvent (8 mL). The mixture was stirred and heated in an oil bath under fluorescent room light irradiation (FL). The cooled reaction mixture was filtered through short silica gel pad, washed with 1 M aq $Na_2SO_3$, dried over $Na_2SO_4$, filtered and concentrated in vacuo. The residue was characterized by $^1$H and $^{13}$C NMR. The results are presented in Table 4.

TABLE 4

Interruption of the halo-de-carboxylation on stage of bromination [a]

| entry | Reaction conditions | yields, % ArBr/ArCl |
|---|---|---|
| 1 | 3-$NCC_6H_4CO_2H$/TCCA 1 mol/$Br_2$ 2 mol/$BrCCl_3$, FL 120° 0.5 h | 84:10 |
| 2 | 4-$NCC_6H_4CO_2H$/TCCA 1 mol/$Br_2$ 2 mol/$BrCCl_3$, FL 120° 0.5 h | 71:6 |

TABLE 4-continued

Interruption of the halo-de-carboxylation on stage of bromination [a]

| en-try | Reaction conditions | yields, % ArBr/ArCl |
|---|---|---|
| 3 | 2-ClC$_6$H$_4$CO$_2$H/TCCA 1 mol/Br$_2$ 2 mol/BrCCl$_3$, FL 120° 0.5 h | 69:28 |
| 4 | 2,4-Cl$_2$C$_6$H$_3$CO$_2$H/TCCA 1 mol/Br$_2$ 2 mol/BrCCl$_3$, FL 120° 0.5 h | 72:24 |
| 5 | 2,4,6-Cl$_3$C$_6$H$_2$CO$_2$H/TCCA 1 mol/Br$_2$ 2 mol/BrCCl$_3$, FL 120° 0.5 h | 75:22 |

[a] All quantities in mole/mole of arenecarboxylic acid. Oil bath temperatures in degrees Celsius.

Example 8

Radical Chlorodecarboxylation of Benzoic Acid Induced by N-Chloroamide and Brominating Agent

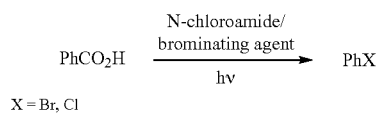

X = Br, Cl

Glass pressure tube filled with benzoic acid (0.8 mmol), N-chloroamide, brominating agent and solvent (4 mL) was magnetically stirred and heated in an oil bath under fluorescent room light irradiation (FL). The yield of chlorobenzene was determined by gas chromatography (GC) using 1-chloro-2-fluorobenzene as internal standard. The results are presented in Table 5.

TABLE 5

N-Chloroamides as reagents for chlorodecarboxylation of benzoic acid [a]

| en-try | Reaction conditions | yield % [b] |
|---|---|---|
| 1 | TCCA 1 mol/Br$_2$ 1 mol/CCl$_4$, FL 100° 6 h | 92 |
| 2 | DCCA 1 mol/Br$_2$ 1 mol/CCl$_4$, FL 100° 6 h | 89 |
| 3 | NCS 1 mol/Br$_2$ 1 mol/CCl$_4$, FL 100° 6 h | 0 |
| 4 | DCDMH 1 mol/Br$_2$ 1 mol/CCl$_4$, FL 100° 6 h | 7 |
| 5 | CPT 1 mol/Br$_2$ 1 mol/CCl$_4$, FL 100° 6 h | 1 |
| 6 | NCSac 1 mol/Br$_2$ 1 mol/CCl$_4$, FL 100° 6 h | 0 |

[a] All quantities in mole/mole of benzoic acid. Oil bath temperatures in degrees Celsius. DCDMH is 1,3-dichloro-5,5-dimethylhydantoin. CPT is N-chlorophthalimide. NCSac is N-chlorosaccharin.
[b] Chlorobenzene analyzed by GC.

Example 9

Chlorodecarboxylation of Benzoic Acid. Optimization of the Reaction Conditions

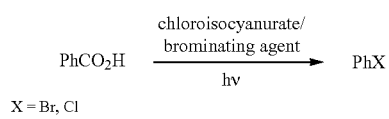

X = Br, Cl

Round bottom flask equipped with Dimroth condenser (chilled to −10° C.) was charged with benzoic acid (0.8 mmol), chloroisocyanurate, brominating agent and solvent (4 mL). The mixture was magnetically stirred and heated in an oil bath under fluorescent room light irradiation (FL). The yields of chloro- and bromobenzenes were determined by gas chromatography (GC) using 1-chloro-2-fluorobenzene as internal standard. The results are presented in Table 6.

TABLE 6

Halo-de-carboxylation of benzoic acid [a]

| En-try | Reaction conditions | GC yield, % PhCl/PhBr |
|---|---|---|
| 1[b] | TCCA 1 mol/Br$_2$ 3 mol/DCM, FL 60° 3 h | 67:0 |
| 2[b] | TCCA 1 mol/Br$_2$ 3 mol/CHCl$_3$, FL 80° 3 h | 82:0 |
| 3[b] | TCCA 1 mol/Br$_2$ 3 mol/CCl$_4$, FL 100° 4 h | 87:7 |
| 4[b] | TCCA 1 mol/Br$_2$ 3 mol/CCl$_4$, FL 100° 5 h | 91:3 |
| 5[b] | TCCA 1 mol/Br$_2$ 3 mol/CCl$_4$, FL 100° 6 h | 92:0 |
| 6[b] | TCCA 1 mol/Br$_2$ 1 mol/CCl$_4$, FL 100° 6 h | 93:0 |
| 7[b] | TCCA 1 mol/Br$_2$ 0.5 mol/CCl$_4$, FL 100° 6 h | 74:1 |
| 8 | TCCA 1 mol/Br$_2$ 1 mol/CCl$_4$, FL 100° 6 h | 75:13 |
| 9 | TCCA 1 mol/Br$_2$ 1 mol/CCl$_4$, FL 100° 6 h | 85:6 |
| 10 | TCCA 1 mol/Br$_2$ 1 mol/CCl$_4$, FL 100° 21 h | 92:0 |
| 11 | TCCA 1 mol/Br$_2$ 0.75 mol/CCl$_4$, FL 100° 21 h | 92:0 |
| 12 | TCCA 1 mol/Br$_2$ 0.6 mol/CCl$_4$, FL 100° 21 h | 90:0 |
| 13 | TCCA 1 mol/Br$_2$ 0.5 mol/CCl$_4$, FL 100° 21 h | 87:0 |
| 14 | TCCA 1 mol/Br$_2$ 0.3 mol/CCl$_4$, FL 100° 21 h | 30:0 |
| 15 | TCCA 1 mol/CCl$_4$, FL 100° 21 h | 0:0 |

[a] All quantities in mole/mole of benzoic acid. Oil bath temperatures in degrees Celsius.
[b] Reaction carried out in glass pressure tube.

Example 10

Exploring the Scope of Chlorodecarboxylation Reaction of Arenecarboxylic Acids $$\text{ArCO}_2\text{H} \xrightarrow[\text{h}\nu]{\text{chloroisocyanurate/ brominating agent}} \text{ArCl}$$

Round bottom flask equipped with Dimroth condenser (chilled to −10° C.) was charged with arenecarboxylic acid (1.8 mmol), chloroisocyanurate, brominating agent and solvent (8 mL). The mixture was magnetically stirred and heated in an oil bath under 3 W LED warm-white lamp irradiation (LL) or under fluorescent room light irradiation (FL). The cooled reaction mixture was filtered through a short silica gel pad, washed with 1 M aq Na$_2$SO$_3$, dried over Na$_2$SO$_4$, filtered and the solvent was removed by distillation. In case of volatile product the yield was determined by gas chromatography (GC) with internal standard. The results are presented in Table 7.

TABLE 7

Chlorodecarboxylation of arenecarboxylic acids ArCO$_2$H [a]

| En-try | ArCO$_2$H | Reaction conditions | yield, % ArCl |
|---|---|---|---|
| 1 | PhCO$_2$H | TCCA 1 mol/Br$_2$ 1 mol/CCl$_4$, 100° FL 18 h | 92[c] |
| 2[b] | 2-FC$_6$H$_4$CO$_2$H | TCCA 1 mol/Br$_2$ 1 mol/CCl$_4$, 100° FL 18 h | 82[c] |
| 3 | C$_6$F$_5$CO$_2$H | TCCA 1 mol/Br$_2$ 1 mol/CCl$_4$, 100° LL 18 h | 75[c] |

TABLE 7-continued

Chlorodecarboxylation of arenecarboxylic acids ArCO$_2$H [a]

| Entry | ArCO$_2$H | Reaction conditions | yield, % ArCl |
|---|---|---|---|
| 4 | 4-Cl-2-FC$_6$H$_3$CO$_2$H | TCCA 1 mol/Br$_2$ 1 mol/CCl$_4$, 100° LL 18 h | 92 |
| 5 | 3-CF$_3$-2-FC$_6$H$_3$CO$_2$H | TCCA 1 mol/Br$_2$ 1 mol/CCl$_4$, 100° LL 18 h | 74 |
| 6 | 2-CF$_3$-5-FC$_6$H$_3$CO$_2$H | TCCA 1 mol/Br$_2$ 1 mol/CCl$_4$, 100° LL 18 h | 61 |
| 7[b] | 3-FC$_6$H$_4$CO$_2$H | TCCA 1 mol/Br$_2$ 1 mol/CCl$_4$, 100° FL 18 h | 89[c] |
| 8 | 5-CF$_3$-3-FC$_6$H$_3$CO$_2$H | TCCA 1 mol/Br$_2$ 1 mol/CCl$_4$, 100° LL 18 h | 59 |
| 9[b] | 4-FC$_6$H$_4$CO$_2$H | TCCA 1 mol/Br$_2$ 1 mol/CCl$_4$, 100° FL 18 h | 92[c] |
| 10[b] | 2-CF$_3$C$_6$H$_4$CO$_2$H | TCCA 1 mol/Br$_2$ 1 mol/CCl$_4$, 100° LL 18 h | 87[c] |
| 11[b] | 2,6-(CF$_3$)$_2$C$_6$H$_3$CO$_2$H | TCCA 1 mol/Br$_2$ 1 mol/CCl$_4$, 100° LL 18 h | 75 |
| 12[b] | 3-CF$_3$C$_6$H$_4$CO$_2$H | TCCA 1 mol/Br$_2$ 1 mol/CCl$_4$, 100° FL 18 h | 100[c] |
| 13 | 3,5-(CF$_3$)$_2$C$_6$H$_3$CO$_2$H | TCCA 1 mol/Br$_2$ 1 mol/CCl$_4$, 100° LL 18 h | 92 |
| 14[b] | 4-CF$_3$C$_6$H$_4$CO$_2$H | TCCA 1 mol/Br$_2$ 1 mol/CCl$_4$, 100° LL 18 h | 100[c] |
| 15[b] | 2-ClC$_6$H$_4$CO$_2$H | TCCA 1 mol/Br$_2$ 1 mol/CCl$_4$, 100° LL 18 h | 87 |
| 16[b] | 2,4-Cl$_2$C$_6$H$_3$CO$_2$H | TCCA 1 mol/Br$_2$ 1 mol/CCl$_4$, 100° FL 18 h | 97 |
| 17 | 2,4,6-Cl$_3$C$_6$H$_2$CO$_2$H | TCCA 1 mol/Br$_2$ 1 mol/CCl$_4$, 100° LL 18 h | 97 |
| 18[b] | 3-ClC$_6$H$_4$CO$_2$H | TCCA 1 mol/Br$_2$ 1 mol/CCl$_4$, 100° LL 18 h | 78 |
| 19 | 3,4-Cl$_2$C$_6$H$_3$CO$_2$H | TCCA 1 mol/Br$_2$ 1 mol/CCl$_4$, 100° LL 18 h | 93 |
| 20 | 4-ClC$_6$H$_4$CO$_2$H | TCCA 1 mol/Br$_2$ 1 mol/CCl$_4$, 100° LL 18 h | 97 |
| 21 | 3-NCC$_6$H$_4$CO$_2$H | TCCA 1 mol/Br$_2$ 1 mol/CCl$_4$, 100° LL 18 h | 93 |
| 22 | 4-NCC$_6$H$_4$CO$_2$H | TCCA 1 mol/Br$_2$ 1 mol/CCl$_4$, 100° LL 18 h | 94 |
| 23 | trimellitic anhydride | TCCA 1 mol/Br$_2$ 1 mol/CCl$_4$, 100° LL 18 h | 86 |

[a] All quantities in mole/mole of benzoic acid. Oil bath temperatures in degrees Celsius.
[b] Reaction carried out in glass pressure tube.
[c] Products analyzed by GC.

Entry 4: 1,4-dichloro-2-fluorobenzene $^1$H NMR: δ 7.30 (m, 1H), 7.15 (dd, 1H, J=9, 2 Hz), 7.43 (d, 1H, J=2 Hz), 7.10 (m, 1H) ppm; $^{13}$C NMR: δ 158.0 (d, J$_{CF}$=252 Hz), 133.3 (d, J$_{CF}$=9 Hz), 131.2, 125.2 (d, J$_{CF}$=4 Hz), 119.8 (d, J$_{CF}$=18 Hz), 117.4 (d, J$_{CF}$=24 Hz) ppm; $^{19}$F NMR: δ-115.3 ppm.

Entry 5: 1-chloro-2-fluoro-3-(trifluoromethyl)benzene $^1$H NMR: δ 7.61 (m, 1H), 7.52 (m, 1H), 7.20 (m, 1H) ppm; $^{13}$C NMR δ 155.7 (dq, J$_{CF}$=259, 2 Hz), 134.6, 125.6 (m), 124.7 (d, J$_{CF}$=5 Hz), 123.0 (d, J$_{CF}$=17 Hz), 122.3 (qd, J$_{CF}$=273, 1.5 Hz), 120.2 (qd, J$_{CF}$=33, 12 Hz) ppm; $^{19}$F NMR: δ-64.7 (d, J$_{FF}$=13 Hz), −119.0 (q, J$_{FF}$=13 Hz) ppm.

Entry 6: 2-chloro-4-fluoro-1-(trifluoromethyl)benzene $^1$H NMR: δ 7.69 (dd, 1H, J=9, 6 Hz), 7.25 (dd, 1H, J=8, 2 Hz), 7.07 (m, 1H) ppm; $^{13}$C NMR: δ 164.4 (d, J$_{CF}$=256 Hz), 134.3 (m), 129.5 (dq, J$_{CF}$=11, 5 Hz), 124.8 (qd, J$_{CF}$=32, 4 Hz), 122.8 (q, J$_{CF}$=273 Hz), 119.3 (d, J$_{CF}$=25 Hz), 114.1 (d, J$_{CF}$=22 Hz) ppm; $^{19}$F NMR δ-65.2, −108.8 ppm.

Entry 8: 1-chloro-3-fluoro-5-(trifluoromethyl)benzene $^1$H NMR: δ 7.43 (s, 1H), 7.29 (m, 1H), 7.25 (m, 1H) ppm; $^{13}$C NMR: δ 162.7 (d, J$_{CF}$=253 Hz), 136.4 (d, J$_{CF}$=10 Hz), 133.8 (qd, J$_{CF}$=34, 9 Hz), 122.8 (qd, J$_{CF}$=273, 4 Hz), 121.9 (dq, J$_{CF}$=4, 4 Hz), 119.9 (d, J$_{CF}$=24 Hz), 111.7 (dq, J$_{CF}$=25, 4 Hz) ppm; $^{19}$F NMR: δ-66.2, −111.3 ppm.

Entry 11: 2-chloro-1,3-bis(trifluoromethyl)benzene $^1$H NMR: δ 7.90 (d, 2H, J=8 Hz), 7.51 (t, 1H, J=8 Hz) ppm; $^{13}$C NMR: δ 131.7 (m), 131.1 (q, J$_{CF}$=32 Hz), 131.0 (q, J$_{CF}$=5 Hz), 127.0, 122.5 (q, J$_{CF}$=274 Hz) ppm; $^{19}$F NMR: δ-66.5 ppm.

Entry 13: 1-chloro-3,5-bis(trifluoromethyl)benzene $^1$H NMR: δ 7.81 (s, 2H), 7.78 (s, 1H) ppm; $^{13}$C NMR: δ 136.2, 133.4 (q, J$_{CF}$=34 Hz), 129.3 (d, J$_{CF}$=3 Hz), 122.7 (q, J$_{CF}$=273 Hz), 120.9 (sept, J$_{CF}$=4 Hz) ppm; $^{19}$F NMR: δ-66.2 ppm.

Entry 15: 1,2-dichlorobenzene $^1$H NMR: δ 7.40 (dd, 2H, J=6, 4 Hz), 7.19 (dd, 2H, J=6, 4 Hz) ppm; $^{13}$C NMR: δ 132.6, 130.6, 127.8 ppm.

Entry 16: 1,2,4-trichlorobenzene $^1$H NMR: δ 7.43 (d, 1H, J=2 Hz), 7.34 (d, 1H, J=9 Hz), 7.16 (dd, 1H, J=9, 2 Hz) ppm; $^{13}$C NMR: δ 133.5, 133.1, 131.2, 131.1, 130.3, 128.0 ppm.

Entry 17: 1,2,3,5-tetrachlorobenzene $^1$H NMR: δ 7.35 (s, 2H) ppm; $^{13}$C NMR: δ 134.8, 132.8, 130.4, 128.7 ppm.

Entry 18: 1,3-dichlorobenzene $^1$H NMR: δ 7.26-7.12 (m, 1H), 7.13-7.09 (m, 3H) ppm; $^{13}$C NMR: δ 135.1, 130.6, 128.8, 127.0 ppm.

Entry 20: 1,4-dichlorobenzene $^1$H NMR: δ 7.27 (s, 1H); $^{13}$C NMR δ 132.6, 129.9 ppm.

Entry 21: 3-chlorobenzonitrile $^1$H NMR: δ 7.64-7.61 (m, 1H), 7.60-7.56 (m, 1H), 7.56-7.53 (m, 1H), 7.42 (t, 1H, J=8 Hz) ppm; $^{13}$C NMR: δ 134.9, 133.1, 131.7, 130.4, 130.2, 117.3, 113.8 ppm.

Entry 22: 4-chlorobenzonitrile $^1$H NMR: δ 7.59 (d, 1H, J=9 Hz), 7.43 (d, 1H, J=9 Hz) ppm; $^{13}$C NMR: δ 139.2, 133.2, 129.5, 117.8, 110.6 ppm.

Entry 23: 4-chlorophthalic Anhydride $^1$H NMR: δ 7.99 (d, 1H, J=8 Hz), 7.96 (s, 1H), 7.90 (d, 1H, J=8 Hz) ppm; $^{13}$C NMR: δ 161.7, 161.5, 143.0, 136.5, 132.8, 129.3, 126.9, 125.8 ppm.

Example 11

Chlorodecarboxylation of o-Bromobenzoic Acid

Glass pressure tube filled with o-bromobenzoic acid (1.8 mmol), TCCA (3.6 mmol), Br$_2$ (3.6 mmol) and CCl$_4$ (8 mL) was magnetically stirred and heated in an oil bath at 100° C. under LED warm-white lamp irradiation for 18 h. The cooled reaction mixture was filtered through a short silica gel pad, washed with 1 M aq Na$_2$SO$_3$, dried over Na$_2$SO$_4$, filtered and the solvent was removed by distillation to give o-dichlorobenzene with 95% yield and 95% purity by GC.

Example 12

Halo-De-Carboxylation of Lauric Acid

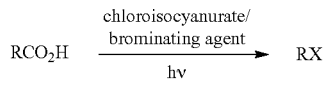

R = n-undecyl; X = Br, Cl

A mixture of lauric acid (0.5 mmol), chloroisocyanurate, brominating agent and solvent (4 mL) was stirred under fluorescent room light irradiation (FL). An aliquot of the reaction mixture washed with 1 M aq Na$_2$SO$_3$, dried over Na$_2$SO$_4$, and filtered through short neutral silica gel pad. The yields of 1-bromo- and 1-chloroundecanes were determined by gas chromatography (GC) using 1,2,4,5-tetrachlorobenzene as internal standard. The results are presented in Table 8.

TABLE 8

Halo-de-carboxylation of lauric acid RCO$_2$H (R is n-undecyl) $^a$

| entry | Reaction conditions | GC yields, % RBr/RCl |
|---|---|---|
| 1 | DCCA 1 mol/[NBu$_4$]Br$_3$ 2 mol/DCM, FL rt 1 h | 29:3 |
| 2 | DCCA 1 mol/[NBu$_4$]Br$_3$ 2 mol/DCM, FL rt 2 h | 54:5 |
| 3 | DCCA 1 mol/[NBu$_4$]Br$_3$ 2 mol/DCM, FL rt 3 h | 72:7 |
| 4 | DCCA 1 mol/[NBu$_4$]Br$_3$ 2 mol/DCM, FL rt 4 h | 81:7 |
| 5 | DCCA 1 mol/[NBu$_4$]Br$_3$ 2 mol/DCM, FL rt 19 h | 67:6 |

$^a$ All quantities in mole/mole of lauric acid.

Example 13

Halo-De-Carboxylation of 4-Chlorophenylacetic Acid

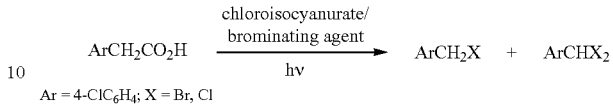

Ar = 4-ClC$_6$H$_4$; X = Br, Cl

A mixture of 4-chlorophenylacetic acid (1 mmol), chloroisocyanurate, brominating agent and solvent (6 mL) was stirred under fluorescent room light irradiation (FL). An aliquot of the reaction mixture washed with 1 M aq Na$_2$SO$_3$, dried over Na$_2$SO$_4$, and filtered through short neutral silica gel pad. The yields of 4-chlorobenzyl bromide and chloride, and 4-chlorobenzal bromide were determined by gas chromatography (GC) using 1,2,4-trichlorobenzene as internal standard. The results are presented in Table 9.

TABLE 9

Halo-de-carboxylation of 4-chlorophenylacetic acid ArCH$_2$CO$_2$H (Ar=4-ClC$_6$H$_4$) $^a$

| entry | Reaction conditions | GC yields, % ArCH$_2$Br/ArCH$_2$Cl/ArCHBr$_2$ |
|---|---|---|
| 1 | TCCA 1 mol/[NBu$_4$]Br$_3$ 1 mol/DCM, FL rt 1 h | 43:9:2 |
| 2 | TCCA 1 mol/[NBu$_4$]Br$_3$ 1 mol/DCM, FL rt 2 h | 42:14:4 |
| 3 | TCCA 1 mol/[NBu$_4$]Br$_3$ 1 mol/DCM, FL rt 2 h | 37:17:12 |
| 4 | DCCA 1 mol/[NBu$_4$]Br$_3$ 1 mol/DCM, FL rt 1 h | 75:5:0 |
| 5 | DCCA 1 mol/[NBu$_4$]Br$_3$ 1 mol/DCM, FL rt 2 h | 80:8:0 |
| 6 | DCCA 1 mol/[NBu$_4$]Br$_3$ 1 mol/DCM, FL rt 3 h | 74:11:3 |
| 7 | DCCA 1 mol/[NBu$_4$]Br$_3$ 1 mol/DCM, FL rt 6 h | 57:21:4 |
| 8 | DCCA 1 mol/[NBu$_4$]Br$_3$ 1 mol/DCM, FL rt 27 h | 22:42:7 |
| 9 | DCCA 1 mol/[NBu$_4$]Br$_3$ 2 mol/DCM, FL rt 0.5 h | 47:1:0 |
| 10 | DCCA 1 mol/[NBu$_4$]Br$_3$ 2 mol/DCM, FL rt 1 h | 80:2:1 |
| 11 | DCCA 1 mol/[NBu$_4$]Br$_3$ 2 mol/DCM, FL rt 2 h | 86:6:1 |

$^a$ All quantities in mole/mole of 4-chlorophenylacetic acid.

Example 14

Comparative Examples

A. Attempts to Chlorodecarboxylate Arenecarboxylic Acids with N-Chlorosuccinimide (NCS) Under Heterolytic Reaction Conditions Disclosed in

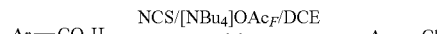

The reactions were provided under fluorescent room lighting (FL).

Example 14A-1. An Attempt to Chlorodecarboxylate Benzoic Acid Using Tetrabutylammonium Trifluororacetate as Catalyst

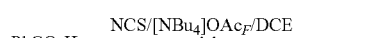

A mixture of benzoic acid (0.44 g, 3.60 mmol), N-chlorosuccinimide NCS (0.46 g, 3.44 mmol), tetrabutylammonium trifluororacetate [NBu$_4$]OAc$_F$ (0.24 g, 0.67 mmol) and 1,2-dichloroethane DCE (6 mL) was stirred at rt for 24 h. The reaction mixture was washed with 1 M aq Na$_2$SO$_3$ (2×10 mL), dried over Na$_2$SO$_4$, and filtered through short neutral alumina pad. The obtained filtrate did not contain chlorobenzene (GC data, 1-chlro-2-fluorobenzene was used as internal standard).

Example 14A-2. An Attempt to Chlorodecarboxylate p-Toluic Acid Using Tetrabutylammonium Trifluororacetate as Catalyst

A mixture of p-toluic acid (0.48 g, 3.52 mmol), N-chlorosuccinimide NCS (0.46 g, 3.44 mmol), tetrabutylammonium trifluororacetate [NBu$_4$]OAc$_F$ (0.24 g, 0.67 mmol) and 1,2-dichloroethane DCE (6 mL) was stirred at rt for 24 h. The reaction mixture was washed with 1 M aq Na$_2$SO$_3$ (2×10 mL), dried over Na$_2$SO$_4$, and filtered through short neutral alumina pad. The obtained filtrate did not contain p-chlorotoluene (GC data, o-dichlorobenzene was used as internal standard).

Example 14A-3. An Attempt to Chlorodecarboxylate p-Anisic Acid Using Tetrabutylammonium Trifluororacetate as Catalyst

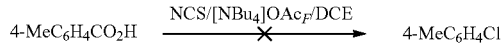

A mixture of p-anisic acid (0.52 g, 3.42 mmol), N-chlorosuccinimide NCS (0.46 g, 3.44 mmol), tetrabutylammonium trifluororacetate [NBu$_4$]OAc$_F$ (0.24 g, 0.67 mmol) and 1,2-dichloroethane DCE (6 mL) was stirred at rt for 24 h. The reaction mixture was washed with 1 M aq Na$_2$SO$_3$ (2×10 mL), dried over Na$_2$SO$_4$, and filtered through short neutral alumina pad. The obtained filtrate did not contain p-chloroanisol (GC data, 1,2,4-trichlorobenzene was used as internal standard).

B. Attempts to Chlorodecarboxylate Arenecarboxylic Acids with N-Chlorosuccinimide (NCS) Under Heterolytic Reaction Conditions Disclosed in *J. Dispersion Sci. Technol.* 2007, v. 28, 613

Example 14B-1: An Attempt to Chlorodecarboxylate 2-Bromobenzoic Acid Using Cetyltrimethylammonium Bromide as Catalyst

A mixture of 2-bromobenzoic acid (0.20 g, 1.0 mmol), N-chlorosuccinimide NCS (0.20 g, 1.5 mmol), cetyltrimethylammonium bromide CTAB (1.82 g, 5.0 mmol) and 1,2-dichloroethane DCE (10 mL) was stirred in dark under reflux conditions for 3 h. The cooled reaction mixture was washed with 1 M aq Na$_2$SO$_3$ (2×5 mL), dried over Na$_2$SO$_4$, filtered through short neutral alumina pad and concentrated in vacuo to give 2-chloroethyl 2-bromobenzoate 2-BrC$_6$H$_4$CO$_2$(CH$_2$)$_2$Cl (0.27 g, 100%). $^1$H NMR: δ 7.85 (d, J=7 Hz, 1H), 7.64 (d, J=7 Hz, 1H), 7.38-7.28 (m, 2H) 4.56 (t, J=6 Hz, 2H), 3.80 (t, J=6 Hz, 2H) ppm.

Example 14B-2: An Attempt to Chlorodecarboxylate 2-Bromobenzoic Acid Using Sodium Dodecyl Sulfate as Catalyst

A mixture of 2-bromobenzoic acid (0.20 g, 1 mmol), N-chlorosuccinimide NCS (0.20 g, 1.5 mmol), sodium dodecyl sulfate SDS (1.44 g, 5.0 mmol) and 1,2-dichloroethane DCE (10 mL) was stirred in the dark under reflux conditions for 3 h. After it was cooled, the reaction mixture was washed with 1 M aq Na$_2$SO$_3$ (2×5 mL), dried over Na$_2$SO$_4$, filtered through short neutral alumina pad and concentrated in vacuo. The residue (15 mg) does not contain 1-bromo-2-chlorobenzene as determined by $^1$H NMR.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A process for the preparation of at least one organic halide of formula (1A) from a carboxylic acid of formula (2A) represented by scheme 1:

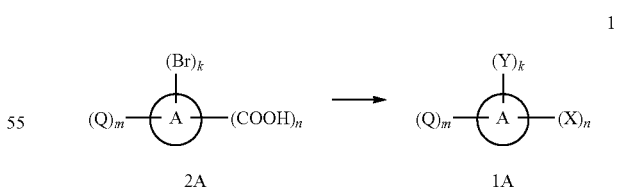

said process comprises radical halo-de-carboxylation reaction comprising reacting carboxylic acid (2A) with a chloroisocyanurate and a brominating agent to yield organic halide (1A);

wherein said chloroisocyanurate is trichloroisocyanuric acid, dichloroisocyanuric acid, or any combination thereof;

A is arene, alkane, cycloalkane or saturated heterocycle;

n is an integer greater than or equal to 1;

X is Cl or Br; wherein if n>1, then X may be the same or different;

k is an integer greater than or equal to 0;

Y is Cl or Br; wherein if k>1, then Y may be the same or different;

m is an integer greater than or equal to 0;

each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;

wherein each $R^1$ is independently aryl, alkyl, cycloalkyl or heterocyclyl, wherein said $R^1$ is optionally substituted by one or more substituents of $R^2$;

wherein each $R^2$ is independently F, Cl, Br, COOH, acyl, aryl, alkyl, cycloalkyl or heterocyclyl; wherein if either one of $R^2$ in (2A) is carboxylic group COOH, then the respective $R^2$ in (1A) is Br or Cl;

wherein the position of said X, Y and Q in said structure of formula (1A) correspond to the same position of said COOH, Br and Q, respectively in said structure of formula (2A).

2. The process of claim 1, wherein A is benzene.

3. The process of claim 1, wherein said organic halide of formula (1A) is a mixture of organic halide products of formula (1A) with different X groups; if k is different than 0, then the organic halide products optionally have also different Y group.

4. The process of claim 1, wherein X and Y in said organic halide (1A) are bromine atoms when A is an alkane, cycloalkane or saturated heterocycle.

5. The process of claim 1, wherein said organic halide is haloarene of formula (1B)

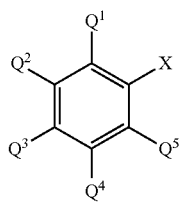

and said carboxylic acid is arenecarboxylic acid of formula (2B)

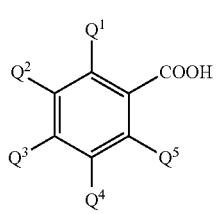

wherein

X is Cl or Br;

each of $Q^1$, $Q^2$, $Q^3$, $Q^4$, and $Q^5$, are independently selected from the group consisting of: H, F, Cl, Br, $R^1$, COOH, acyl, $C(O)R^1$, acetyl, benzoyl, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, and $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;

wherein each $R^1$ is independently aryl, alkyl, cycloalkyl or heterocyclyl; wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Cl or Br;

wherein if either one of $Q^1$, $Q^2$, $Q^3$, $Q^4$, $Q^5$, and/or $R^2$ in (2B) is bromine (Br) then the respective $Q^1$, $Q^2$, $Q^3$, $Q^4$, $Q^5$, and/or $R^2$ in (1B) is Cl or Br.

6. The process of claim 5, wherein if either one of $Q^1$, $Q^2$, $Q^3$, $Q^4$, $Q^5$ is a nitro group, then X is Br or if none of the substituents $Q^1$, $Q^2$, $Q^3$, $Q^4$ and $Q^5$ are a nitro group, then X is Cl.

7. The process of claim 6, wherein if none of the substituents $Q^1$, $Q^2$, $Q^3$, $Q^4$ and $Q^5$ area nitro group and if either one of $Q^1$, $Q^2$, $Q^3$, $Q^4$, or $Q^5$ in arenecarboxylic acid (2B) is Br then the respective $Q^1$, $Q^2$, $Q^3$, $Q^4$, or $Q^5$ in haloarene (1B) is Cl.

8. The process of claim 5, wherein at least one of $Q^1$, $Q^2$, $Q^3$, $Q^4$, and/or $Q^5$ is F, Cl, Br, $CF_3$, $CCl_3$, CN, COOH, C(O)OMe, $NO_2$, $OCF_3$, and/or any two of $Q^1$ and $Q^2$, $Q^2$ and $Q^3$, $Q^3$ and $Q^4$, or $Q^4$ and $Q^5$, are joined to form a dihydrofuran-2,5-dione or pyrrolidine-2,5-dione ring.

9. The process of claim 1, wherein the ratio between said chloroisocyanurate:(each carboxylic group of the carboxylic acid of formula (2A)) is between 0.1 and 2.

10. The process of claim 1, wherein said brominating agent is $Br_2$ (bromine), a salt containing bromide or polybromide anion and organic or inorganic cation; or any combination thereof.

11. The process of claim 10, wherein said polybromide anion is an ion of formula $$[Br_p]^{q-}$$

where p is an integer of at least 3 and q is an integer of at least 1 and not more than p/2.

12. The process of claim 1, wherein the molar ratio between said brominating agent:(each carboxylic group of the carboxylic acid of formula (2A)) is between 0.1 and 4.

13. The process of claim 1, wherein said reaction is conducted at a temperature of between −20° C. and 200° C.

14. The process of claim 1, wherein in order to accelerate the radical reaction the reaction mixture is subjected to electromagnetic irradiation.

15. The process of the claim 14, wherein said electromagnetic irradiation is microwave, infrared, ultraviolet, or visible light irradiation or any combination thereof.

16. The process of claim 1, wherein said reaction is conducted in the presence of radical initiator.

17. The process of claim 16, wherein said radical initiator is an azo compound or organic peroxide.

18. A radiation-sensitive composition comprising a carboxylic acid (2A)

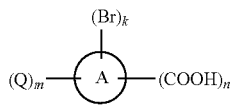

a chloroisocyanurate and a brominating agent which generates organic halide (1A)

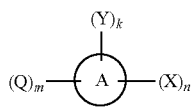

upon electromagnetic irradiation,
wherein
said chloroisocyanurate is trichloroisocyanuric acid, dichloroisocyanuric acid, or any combination thereof;

A is arene, branched alkane, cycloalkane or saturated heterocycle;

n is an integer greater than or equal to 1;

X is Cl or Br; wherein if n>1, then X may be the same or different;

k is an integer greater than or equal to 0;

Y is Cl or Br; wherein if k>1, then Y may be the same or different;

m is an integer greater than or equal to 0;

each Q is independently F, Cl, Br, $R^1$, acyl, $C(O)R^1$, $C(O)OR^1$, $C(O)OMe$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;

wherein each $R^1$ is independently aryl, alkyl, cycloalkyl or heterocyclyl, wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $R^2$ in (2A) is a carboxylic group COOH, then the respective $R^2$ in (1A) is Br or Cl;

wherein the position of said Br and Q in said structure of formula (1A) correspond to the same position of said COOH and Q, respectively in said structure of formula (2A).

19. The composition of claim 18, wherein X and Y in said organic halide (1A) are bromine atoms when A is an alkane, cycloalkane or saturated heterocycle.

20. The composition of claim 18, wherein A is benzene.

21. The composition of claim 18, wherein said carboxylic acid is arenecarboxylic acid of formula (2B)

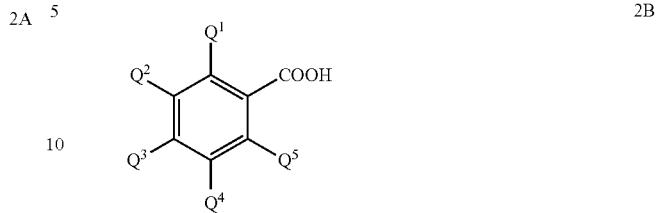

and said organic halogen is haloarene of formula (1B)

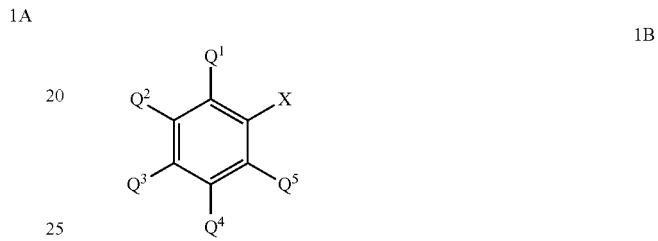

wherein
X is Cl or Br;
wherein $Q^1$, $Q^2$, $Q^3$, $Q^4$, and $Q^5$, are each independently selected from the group consisting of: H, F, Cl, Br, $R^1$, COOH, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, and $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;

wherein each $R^1$ is independently aryl, alkyl, cycloalkyl or heterocyclyl wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Cl or Br;

wherein if either one of $Q^1$, $Q^2$, $Q^3$, $Q^4$, $Q^5$, and/or $R^2$ in (2B) is bromine (Br) then the respective $Q^1$, $Q^2$, $Q^3$, $Q^4$, $Q^5$, and/or $R^2$ in (1B) is Cl or Br.

22. The composition of claim 21, wherein if either one of $Q^1$, $Q^2$, $Q^3$, $Q^4$ or $Q^5$ is a nitro, then X is Br.

23. The composition of claim 21, wherein if none of the substituents $Q^1$, $Q^2$, $Q^3$, $Q^4$ and $Q^5$ are a nitro group, then X is Cl or if either one of $Q^1$, $Q^2$, $Q^3$, $Q^4$, or $Q^5$ in arenecarboxylic acid (2B) is Br then the respective $Q^1$, $Q^2$, $Q^3$, $Q^4$, or $Q^5$ in haloarene (1B) is Cl.

24. The composition of claim 18, wherein the molar ratio of said chloroisocyanurate:(each carboxylic group of the carboxylic acid of formula (2A)) molar ratio is between 0.1 and 2.

25. The composition of claim 18, wherein said brominating agent is $Br_2$ (bromine), a salt containing bromide or polybromide anion and organic or inorganic cation; or any combination thereof.

26. The composition of claim 25 wherein said polybromide anion is an ion of formula $$[Br_p]^{q-}$$

where p is an integer of at least 3 and q is an integer of at least 1 and no more than p/2.

27. The composition of claim 18, wherein the brominating agent/(each carboxylic group of the carboxylic acid of formula (2A)) molar ratio is between 0.1 and 4.

28. The composition of claim 18, wherein electromagnetic irradiation is microwave, infrared, ultraviolet, or visible light irradiation or any combination thereof.

* * * * *